United States Patent [19]
Sijmons et al.

[11] Patent Number: 5,866,777
[45] Date of Patent: Feb. 2, 1999

[54] METHOD FOR OBTAINING PLANTS WITH REDUCED SUSCEPTIBILITY TO PLANT-PARASITIC NEMATODES

[75] Inventors: Peter Christiaan Sijmons, Amsterdam; Oscar Johannes Maria Goddijn, Leiden; Petrus Josephus Maria Van Den Elzen, Voorhout; Frédérique Marianne Van Der Lee, Leidschendam, all of Netherlands

[73] Assignee: Mogen International, N.V., Leiden, Netherlands

[21] Appl. No.: 244,122

[22] PCT Filed: Nov. 2, 1992

[86] PCT No.: PCT/EP92/02559

§ 371 Date: May 19, 1994

§ 102(e) Date: May 19, 1994

[87] PCT Pub. No.: WO93/10251

PCT Pub. Date: May 27, 1993

[30] Foreign Application Priority Data

Nov. 20, 1991 [EP] European Pat. Off. ............. 91203041
Jan. 10, 1992 [EP] European Pat. Off. ............. 92200046

[51] Int. Cl.⁶ ................... C12N 15/09; C12N 15/29; C12N 15/82; A01H 4/00
[52] U.S. Cl. .............. 800/205; 536/23.6; 536/23.7; 536/24.1; 435/172.3; 435/252.3; 435/320.1
[58] Field of Search ................... 800/205; 536/23.6, 536/23.7, 24.1; 435/172.3, 252.3, 320.1

[56] References Cited

U.S. PATENT DOCUMENTS

| | | | |
|---|---|---|---|
| 4,940,840 | 7/1990 | Suslow et al. | 800/205 |
| 4,970,168 | 11/1990 | Tumer | 435/317.1 |
| 5,236,843 | 8/1993 | Narua et al. | 435/252.3 |

FOREIGN PATENT DOCUMENTS

| | | |
|---|---|---|
| 0303426 | 2/1989 | European Pat. Off. |
| 0412911 | 8/1989 | European Pat. Off. |
| 9204453 | 3/1992 | WIPO |
| 9221757 | 12/1992 | WIPO |

OTHER PUBLICATIONS

Gurr, S. J., et al. 'Gene expression in nematode–infected plant roots.' MGG Molecular and General Genetics, vol. 226, No. 3, May 1991, Berlin D, pp. 361–366.
Niebel, A., et al. 'Molecular Analysis of Nematode–Induced Giant Cells in Potato Roots.' Journal of Cellular Biochemistry Supplement, vol. 13D, 1989, New York, p. 323.
Gurr, S.J., et al. 'Identification of Plant Genes Expressed at the Feeding Site of the Potato Cyst Nematode.' Journal of Cellular Biochemistry Supplement, vol. 15 A, 1991, New York, p. 56.
Botterman et al 1988 Trends in Genetics 4 (8):219–222.
Influence of Changes in the Nurse Cell System . . . F. Grundler, et al Phytopathology vol. 81 No. 1, 1991 pp. 70–74.

*Primary Examiner*—Douglas W. Robinson
*Assistant Examiner*—Thomas Haas
*Attorney, Agent, or Firm*—Ladas & Parry

[57] ABSTRACT

A method for obtaining plants with reduced susceptibility to invasion by a plant parasitic nematode, and plants having reduced susceptibility to invasion by a plant parasitic nematode obtained, for example, with such method. The method includes the following steps: (a) transforming cells of a plant or progeny of the plant with a coding sequence A and a coding sequence B, the coding sequences A and B being selected such that transformed cells expressing the coding sequences A and B display a normal phenotype and such that a nematode feeding structure comprising a cell expressing the coding sequence A but not expressing the coding sequence B has a reduced ability to support development of the plant parasitic nematode as compared with a nematode feeding structure wherein coding sequence A is not expressed, the coding sequence A being under the control of a promoter A that drives expression of the coding sequence A preferentially in the cell of the nematode feeding structure, the coding sequence B being under the control of a promoter B that drives expression of the coding sequence B in transformed cells wherein coding sequence A is expressed but not in the cell of the nematode feeding structure; (b) generating plants from the transformed cells of step (a); and (c) screening the generated plants for a transformed plant which has a reduced susceptibility to the plant parasitic nematode and which displays the normal phenotype.

22 Claims, 16 Drawing Sheets pMOG711 = NADPH-CytP450 reductase ATR1 pMOG712 = NADPH-CytP450 reductase ATR2 pMOG713 = G3P acyltransferase ATS1 pMOG714 = adenine nucleotide translocator pMOG715 = β subunit ATP synthase

METHOD FOR OBTAINING PLANTS WITH REDUCED SUSCEPTIBILITY TO PLANT-PARASITIC NEMATODES

TECHNICAL FIELD

This invention concerns plants with reduced susceptibility to plant-parasitic nematodes and methods for obtaining same involving recombinant DNA technology.

BACKGROUND OF THE INVENTION

Plant-parasitic nematodes worldwide cause diseases of nearly all crop plants of economic importance with estimated losses of about $ 5.8 billion/yr in the Unites States alone (Sasser and Freckman, 1987, World prospective on nematology In: Vistas on Nematology, Eds. Veech & Dickson. Hyatts Will, Md. pp. 7–14). While in tropical regions losses caused by nematodes are due mainly to root-knot nematodes (Meloidogyne), in Europe cyst nematodes of the genera Globodera and Heterodera are regarded as serious pests and important limiting factors in e.g. potato, rapeseed and sugarbeet cultivation, respectively. Only a small number of resistant crop varieties have emerged from breeding programmes for e.g. potato, sugarbeet, tomato, soybean and oil radish (Dropkin, 1988, Ann. Rev. Phytopath. 26, 145–161; Trudgill, 1991, Ann. Rev. Phytopath. 29, 167–192). The resistance is often based on single R-genes (Rick & Fobes, 1974, Tomato Gen. Coop. 24, 25; Barone et al. 1990, Mol. Gen. Genet. 224, 177–182) and leads to breakdown of resistance after several generations (Shidu & Webster, in: Plant Parasitic Nematodes, Vol. III, 1981, Zuckerman et al. (eds.) Acad. Press, New York, pp 61–87; Turner, 1990, Ann. Appl. Biol. 117, 385–397).

Plant-parasitic nematodes are obligate parasites. Nematodes such as cyst and root-knot nematodes are completely dependent on the formation of proper feeding structures inside the plant root. These feeding structures arise from single root cells that are selected by the nematode after invasion of the root. In the case of cyst nematodes, the IFC (initial feeding cell) develops into a syncytium through digestion of cell walls and hypertrophy. After infection with a root-knot nematode, the IFC develops into a giant cell through several nuclear divisions without cytokinesis and becomes metabolically very active. During establishment of the feeding structure, the infective juvenile nematode becomes immobile and loses the ability to move to other feeding sites, illustrating their dependance on the induced nematode feeding structure (NFS).

Clearly, there is a great need for plants with reduced susceptibility to plant parasitic nematodes. Current strategies to combat pathogens and pests involve expression of recombinant DNA encoding a product which has a direct interaction with the pathogen or pest.

EP-A 159 884 teaches the expression in plants of a gene encoding an insecticidal toxin of *Bacillus thuringiensis*. Once the protein is digested by the insect it binds to a receptor in the gastrointestinal tract, eventually resulting in the death of the insect. The interaction of the toxin and a receptor in the insect is crucial to the toxic effect, which may explain the relatively frequent instances of acquired resistance to the toxin.

EP-A 303 426 reports that a number of *B. thuringiensis* strains act on nematodes. It is therefore not surprising that the suggestion is made to identify the genes that encode for these nematicidal toxins and express these genes in plants to protect them from nematodes (EP-A 352 052).

However, it is of some concern that the direct interaction between toxin and pest is prone to the swift development of resistance, as has been reported for *B. thuringiensis* endotoxin (Peferoen M. (1991) Agroindustry High-Tech , p. 5–9.

It is therefore an object of the present invention to provide plants with reduced susceptibility to pathogens and pests which avoids the problem of acquired resistance altogether.

SUMMARY OF THE INVENTION

The present invention provides plants which as a result of the expression of a recombinant DNA have reduced susceptibility to plant-parasitic nematodes. According to a preferred embodiment said recombinant DNA causes disruption of a nematode feeding structure. In another preferred embodiment expression of said recombinant DNA is at least retarding formation of a nematode feeding structure. According to a more preferred embodiment said recombinant DNA comprises:

1) a gene-A which upon expression effects disruption of a nematode feeding structure, said gene-A being placed under the control of a promoter-A that drives expression at least in the nematode feeding structure, and
2) a gene-B which upon expression neutralizes the disruptive effect of gene-A, said gene-B being placed under the control of a promoter-B that drives expression in substantially all of the plant's cells wherein gene-A is expressed, with the proviso that said promoter does not effectively drive expression of gene-B in the nematode feeding structure. A preferred gene-A encodes barnase, while gene-B encodes barstar, and wherein promoter-A is a resident plant promoter and promoter-B is obtainable from the CaMV 35S promoter or the rolD promoter. In another embodiment promoter-A is a promoter that is isolated from a plant, or a derivative from the said promoter. A preferred promoter according to this embodiment is a promoter-A obtainable from the Delta-0.3TobRB7-5A promoter or a truncated rolC promoter.

According to another aspect of the invention said recombinant DNA comprises a gene inhibitory to an endogenous gene that encodes a protein or polypeptide product that is essential for formation or maintenance of a nematode feeding structure. Preferred according to this aspect of the invention is a gene-A which produces a RNA transcript that is complementary to an endogenous gene transcript encoding a protein or polypeptide product essential for formation or maintenance of a nematode feeding structure, in particular a gene that is essential for cell viability, and wherein said gene-B encodes a protein or polypeptide product that substitutes the function of the protein or polypeptide encoded by the said endogenous gene. Said neutralizing gene is preferably obtainable from a heterologous gene of a different species, such as a plant species, animal species, or microbial species; preferably a different plant species. Highly preferred genes that are essential to cell viability according to this invention are those encoding a protein or polypeptide which is selected from the group consisting of ATP synthase, adenine nucleotide translocator, tricarboxylate translocator, dicarboxylate translocator, 2-oxo-glutarate translocator, cytochrome C, pyruvate kinase, glyceraldehyde-3P-dehydrogenase, NADPH-cytochrome p450 reductase, fatty acid synthase complex, glycerol-3P-acyltransferase, hydroxymethyl-glutaryl CoA reductase, aminoacyl transferase, transcription initiation factor, and transcription elongation factor.

A preferred plant according to the invention is one from the family Solanaceae, more preferably *Solanum tuberosum*, potato, still more preferred is a potato plant which has reduced susceptibility to a potato cyst nematode.

The invention also encompasses plant material, such as flowers, fruit, leaves, pollen, seeds, or tubers, obtainable from a plant according to the invention.

The invention also provides methods for obtaining a plant with reduced susceptibility to a plant parasitic nematode, comprising the steps of
(1) transforming a recipient plant cell with recombinant DNA which comprises (a) a gene which when expressed in a nematode feeding structure causes disruption thereof and (b) a plant selectable marker gene,
(2) generating a plant from a transformed cell under selection pressure,
(3) selecting a transformed plant with reduced susceptibility to a plant parasitic nematode.

The invention further comprises a method for obtaining a plant with reduced susceptibility to a plant parasitic nematode, comprising the steps of:
(1) transforming a recipient plant cell with recombinant DNA which comprises (a) a gene-A which upon expression effects disruption of a nematode feeding structure, said gene-A being placed under the control of a promoter-A that drives expression at least in the nematode feeding structure, and (b) a gene-B which upon expression neutralizes the disruptive effect of gene-A, said gene-B being placed under the control of a promoter-B that drives expression in substantially all of the plant's cells wherein gene-A is expressed, with the proviso that said promoter does not effectively drive expression of gene-B in the nematode feeding structure, and (c) a plant selectable marker gene,
(2) generating a whole plant from a transformed cell under selection pressure,
(3) identifying a transformed plant with reduced susceptibility to said plant parasitic nematode.

According to a slightly different embodiment a method for obtaining a plant with reduced susceptibility to a plant parasitic nematode is provided, comprising the steps of:
(1) transforming a recipient plant cell with recombinant DNA which comprises (a) a gene-B which upon expression neutralizes the disruptive effect of a gene-A to be introduced in step (3), said gene-B being placed under the control of a promoter-B that drives expression in substantially all of the plant's cells wherein gene-A is expressed, with the proviso that said promoter does not effectively drive expression of gene-B in a nematode feeding structure, and (b) a plant selectable marker,
(2) generating a whole plant from a transformed cell under selection pressure,
(3) transforming a recipient cell of the plant obtained in step (2), or progeny thereof, which at least contains gene-B, with a recombinant DNA which comprises (c) a gene-A which upon expression effects disruption of a nematode feeding structure, said gene-A being placed under the control of a promoter-A that drives expression at least in a nematode feeding structure of an infected plant root,
(4) generating a plant from a cell transformed in step (3) under the appropriate selection pressure,
(5) identifying a plant that has reduced susceptibility to a plant parasitic nematode.

A preferred method for transforming a recipient plant cell is by coincubating said cell with an Agrobacterium strain that contains said recombinant DNA.

The invention further provides recombinant DNA containing a plant expressible gene which comprises in sequence:

a promoter-A that drives expression of a downstream gene in a nematode feeding structure,
a gene-A which when expressed in a nematode feeding structure effects the disruption thereof, and optionally,
a transcription terminator and a polyadenylation signal sequence, so linked that the said gene-A is expressed in said nematode feeding structure. In a preferred recombinant DNA according to the invention said promoter is obtainable from the Delta-0.3TobRB7-5A or the truncated rolC promoter. Also preferred in a recombinant DNA according to the invention is a gene-A obtainable from the Barnase gene from *Bacillus amyloliauefaciens*.

According to another preferred embodiment a recombinant DNA is provided wherein the said gene-A is obtainable from a host plant and selected from the group consisting of those encoding ATP synthase, adenine nucleotide translocator, tricarboxylate translocator, dicarboxylate translocator, 2-oxo-glutarate translocator, cytochrome C, pyruvate kinase, glyceraldehyde-3P-dehydrogenase, NADPH-cytochrome p450 reductase, fatty acid synthase complex, glycerol-3P-acyltransferase, hydroxymethylglutaryl CoA reductase, aminoacyl transferase, transcription initiation factor, and transcription elongation factor, said gene being fused to the said promoter in the reverse orientation with respect to the natural orientation in the host plant.

The invention further provides plant transformation vectors containing recombinant DNA according to the inventionan, as well as Agrobacterium strains containing said plant transformation vectors.

Especially Preferred vectors for use in a process according to the invention may be selected from the group consisting of pMOG716, pMOG719, pMOG589, pMOG699, pMOG717, pMOG711, pMOG712, pMOG713, pMOG714, pMOG715, pMOG718 and pMOG720, and derivatives thereof modified in a way not essential to the invention.

The invention further provides methods for reducing damage to crops by plant parasitic nematodes by growing plants according to the invention.

According to another aspect of the invention a method for reducing damage to crops by plant parasitic nematodes is provided which comprises growing a plant that contains a herbicide resistance gene placed under the control of a promoter-B that is expressed in substantially all of the plant's root cells wherein gene-A is expressed, with the proviso that it does not effectively drive expression in the NFS, comprising the steps of
1) growing the said plant,
2) contacting the roots of said plant with a herbicide.

The meaning of the expressions used herein, as well as the application and the advantages of the invention will become clear from the following detailed description of the invention.

DETAILED DESCRIPTION OF THE INVENTION

Figure 1:
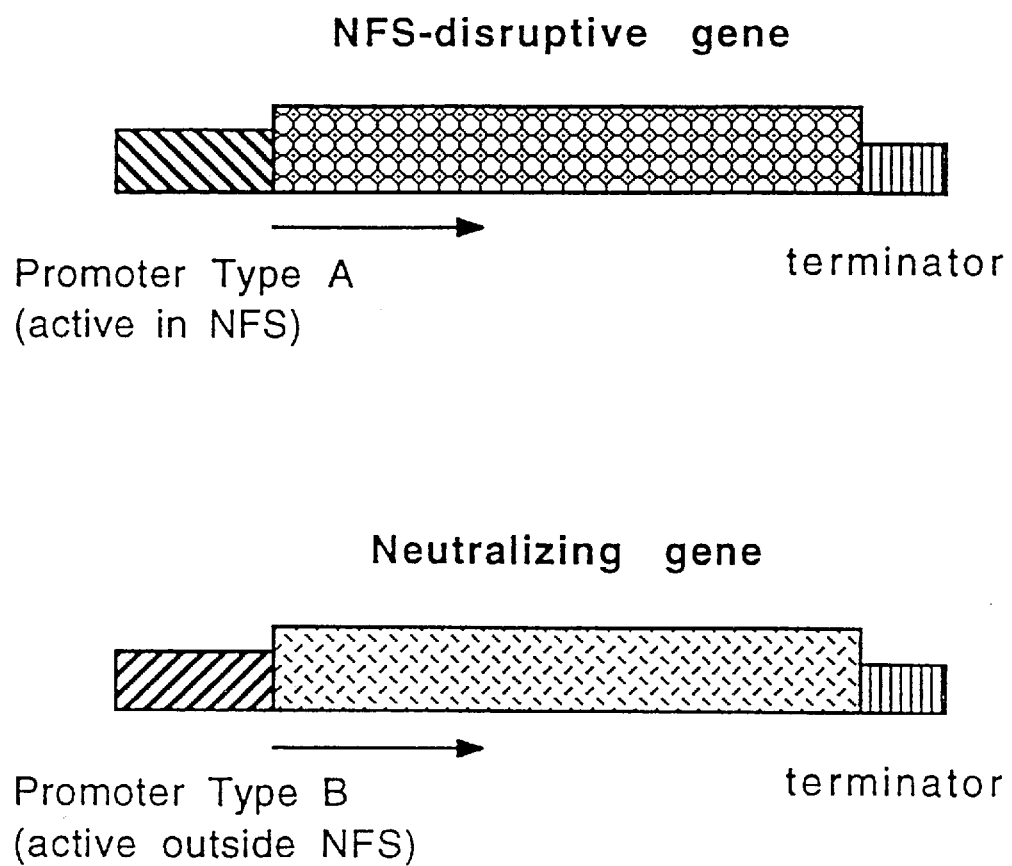
FIG. 1. Schematic representation of the Two-component Resistance Strategy as outlined in this invention.

It has now been surprisingly found that a plant can be made less susceptible to a plant-parasitic nematode by disrupting the nematode feeding structure via the expression of a barnase gene under the control of a promoter that is active inside the NFS, while the potentially disruptive activity to plant cells outside the NFS was shown to be effectively impaired by the concurrent expression of barstar under the control of the CaMV 35S promoter. These plants do not have the disadvantage that the plant parasitic nematodes can acquire resistance against a toxic substance used for the defense, since the direct interaction between the pathogen or pest and the toxin does not play a role in the defense of the plant.

The following surprising findings illustrate how the invention can be worked in a number of alternative ways.

When the CaMV 35S promoter (Guilley et al., 1982, Cell 30, 763–773), which in healthy plants gives rise to high expression of the GUS gene in root cells and especially the vascular cylinder (Benfey et al. (1990) EMBO J. 9, 1677–1684) is used to drive the expression of the GUS-gene in nematode infected plants, a remarkable absence of GUS-activity is observed inside nematode feeding structures (NFS). This was tested for three plant species, Arabidonsis, tobacco and potato infected with representative species of PPN (*H. schachtii, M. incognita, G. tabacum, G. rostochiensis* respectively) and allowed to form NFS. Other promoters that give rise to high GUS expression in root tissue (Leach & Aoyagi1991, Plant Sci. 79, 69–76), including epidermis cells and root hairs, are the rolC and rolD promoter sequences from plasmid pRiA4 of *Agrobacterium rhizogenes* (5' flanking region of open reading frames 12 and 15 respectively, in Slightom et al. (1986, J. Biol. Chem. 261, 108–121). Also with these promoters, a surprisingly strong suppression of GUS activity was observed inside NFS after infection with PPN.

In contrast with the above findings, a truncated version of the rolC-promoter derived from the nucleotide sequence 11286 up to 12132 between the open reading frames 11 and 12 of the TL-DNA from an *Agrobacterium rhizogenes* plasmid pRiA4 (Slightom et al. 1986, J. Biol. Chem. 261, 108–121) remains active inside the NFS, as was observed after fusion of the truncated rolc-promoter to the GUS gene and transformation of Arabidonsis with this construct. Apparently, part of the promoter is sensitive to down-regulation during NFS development and, once this part is removed, the promoter is no longer suppressed in the NFS.

Plants were transformed with a recombinant DNA construct on a binary vector from Agrobacterium containing a promoterless GUS-gene cloned directly adjacent to the right border within the T-DNA in the direction pointing away from the right border and a second selectable marker. Regenerants were grown on selective media, grown to maturity and allowed to set seed. Plants obtained from the seed were grown and after infection and formation of NFS, the roots were assayed for GUS-activity. A rather unexpected number of plant lines were detected with GUS activity inside the NFS. However, no plant lines were found that contain GUS-activity in the NFS only; all plant lines showed at least some GUS activity in non-NFS plant parts. Furthermore, most of the plant lines with a promoterless GUS construct that showed GUS activity inside the vascular cylinder of healthy roots, also demonstrated a down-regulation of GUS activity during development of the NFS.

We conclude that with a reasonable frequency one is capable of obtaining plant lines which express any promoterless gene inside the NFS of an infected plant using the approach illustrated with the promoterless GUS-gene. It can also be inferred from these experiments that promoters that are truly specific for the NFS are at least very rare.

Moreover, the lack of GUS-enzyme activity in the NFS is inevitably caused by the down-regulation of the CaMV 35S promoter inside the NFS.

The findings set out above, i.e. that a promoter which is active inside the NFS can with a reasonable frequency be tagged using a promoterless gene-construct and the fact that the 35S promoter was shown to be down regulated inside the NFS it was concluded that the mosaic expression patterns can be used to obtain plants with reduced susceptibility to PPN by the approach outlined below.

Step I Plants are transformed with recombinant DNA which
   comprises (a) a gene-B coding for a neutralizing substance such as barstar, fused behind a promoter-B with the property that it is in general constitutive but is down-regulated during the development of the feeding structure and (b) a plant selectable marker. Regenerants on selection media may be screened for expression of gene-B using e.g. Western detection techniques. Plants expressing gene-B are grown to maturity and allowed to set seed from which a second generation of plant can be generated (T2).

Step II The T2 generation is used for a second round of transformation, now with recombinant DNA which comprises a promoterless gene-A coding for a disruptive substance, like barnase or a gene inhibitory to a gene essential to cell viability according to the invention, cloned directly adjacent to the right border within the T-DNA in the direction pointing away from the right border, and a second selectable marker. (The plant selectable marker gene may or may not be different from the one used in the first round of transformation, depending on whether that gene is still present or functional in the T2. Methods to remove or inactivate plant selectable markers are known in the art (e.g. as disclosed in WO92/01370). Regenerants are grown on selective media, grown to maturity and allowed to set seed from which the next generation of plants are grown (T3).

Step III The next generation (T3) is screened for decreased susceptibility to PPN and, optionally, absence of deviant growth and development. Due to the randomness of integration the second round of transformation occasionally results in integration of the promoterless gene-A into regions of the plant genome that is capable of actively promoting transcription of gene-A inside the NFS. The screening after PPN infection results in plants that express sufficiently gene-A inside the feeding structures to prevent full development of these structures and which are unable to support complete life cycles of PPN, while on the other hand, a possible expression of gene-A in other areas besides the feeding structure is neutralized by the concomittant expression of gene-B.

In more generalized terms the invention provides a method for obtaining plants which show a reduced susceptibility to PPN, comprising the steps of effecting the integration into the genome of the said plant of 1) a gene-A which upon expression effects disruption of a nematode feeding structure, said gene being placed under the control of a promoter-A that is at least expressed in the NFS, and 2) a gene-B which upon expression neutralizes the disruptive effect of gene-A, said gene-B being placed under the control of a promoter-B that drives expression in substantially all of the plant's cells but not effectively in the NFS, and 3) selecting the plants that show reduced susceptibility to PPN.

The advantages and the numerous ways of working the invention will be appreciated from the following detailed description of the invention.

For the purpose of this invention, it is important to note that there are no absolute requirements for each of the promoters-A and -B separately, i.e. promoter-B need not be active in every plant cell outside the NFS at all stages of development but has to be active at least in those plant cells outside the feeding structure where the promoter-A shows leaky activity to such a degree that expression of the disruption gene is impairing plant viability in areas outside the nematode feeding structure. Likewise, the promoter-A does not have to be entirely specific for the NFS as long as activity in other plant cells at any stage of plant development is counteracted by concurrent activity of gene-B products in those cells. Promoter-B may even show some degree of leaky activity inside the NFS as long as the expression of gene-B is sufficiently low to allow the detrimental effect of gene-A products inside the NFS.

A suitable promoter-A, that is active inside NFS but inactive in as much other tissues as possible can be identified using techniques as described in this application. After identification and isolation of such a promoter-A, it can be fused in front of a disruptive gene-A and used in the second round of transformation as described in Phase II. The resulting plant lines, transgenic both for promoter-A/gene-A and promoter-B/gene-B, can be analyzed for reduced susceptibility to PPN as described in this specification.

Alternatively, both the constitutive promoter-B/gene-B and the NFS promoter-A/gene-A constructs can be placed on the same vector and used for a single round of plant transformation. Regenerants on selective media are grown to maturity. The next generation of plants can be screened directly for decreased susceptibility to PPN and absence of deviant growth and development.

According to another aspect of the invention the NFS-specific repression of a constitutive promoter-B according to the invention may be used to make plants resistant to a herbicide or antibiotic, yielding plants that are locally, i.e inside the NFS, susceptible to compounds with a herbicidal or antibiotic activity. Suitable herbicide resistance genes, capable of neutralizing a herbicidal effect, which are to be fused to a promoter-B according to the invention, can readily be selected by those of skill in the art; they include, but are not limited to, the herbicide resistance genes mentioned as selection marker below. Suitable selectable marker genes that can be used to select or screen for transformed cells, may be selected from any one of the following non-limitative list: neomycin phosphotransferase genes conferring resistance to kanamycin (EP-B 131 623), the hygromycin resistance gene (EP 186 425 A2) the Glutathione-S-transferase gene from rat liver conferring resistance to glutathione derived herbicides (EP-A 256 223), glutamine synthetase conferring upon overexpression resistance to glutamine synthetase inhibitors such as phosphinothricin (WO87/05327), the acetyl transferase gene from *Streptomyces viridochromogenes* conferring resistance to the selective agent phosphinothricin (EP-A 275 957), the gene encoding a 5-enolshikimate-3-phosphate synthase (EPSPS) conferring tolerance to N-phosphonomethylglycine, the bar gene conferring resistance against Bialaphos (e.g. WO91/02071), and the like. The actual choice of the marker is not crucial as long as it is functional (i.e. selective) in combination with the plant cells of choice.

The marker gene and the gene of interest do not necessarily have to be linked, since co-transformation of unlinked genes (U.S. Pat. No. 4,399,216) is also an efficient process in plant transformation.

The present invention also provides vectors which comprise recombinant DNA for the stable transformation of plants, containing:

(a) a screenable gene for studying promoter activity and isolating a suitable promoter-A and/or promoter-B (pMOG452), (b) suitable neutralizer genes according to the invention under the control of a promoter-B (pMOG583, pMOG716, pMOG719), (c) disrupter genes according to the invention which either have no promoter of themselves and can be used for a second round of transformation to become integrated downstream of a suitable promoter-A according to the invention resident in the genome of a plant which already contains a neutralizer gene, (pMOG589), or (d) disrupter genes according to the invention which are under the control of an isolated promoter-A according to the invention, (pMOG699, pMOG717, pMOG711, pMOG712, pMOG713, pMOG714, pMOG715) which can be used for a second round of transformation or co-transformation with a vector containing a neutralizer gene under the control of a promoter-B according to the invention, (e) suitable combinations of disrupter and neutralizing genes according to the invention, wherein the disrupter gene may be promoterless (pMOG718), or downstream of an isolated promoter-A, (pMOG718; pMOG720 and derivatives), which may be used to transform plants in a single round of transformation and of which a number has reduced resistance to plant parasitic nematodes.

Within the context of this invention, the terms NFS disruptive substance and neutralizing substance embraces a series of selected compounds that are encoded by DNA whose gene products (either protein or RNA or antisense-RNA) are detrimental to the metabolism and/or functioning and/or viability of NFS or organelles therein and for which neutralizing substances are known that are able, when expressed simultaneously in the same cell as the disruptive substance, to repress the activity of the disrupting substance. Preferable combinations of disrupting and neutralizing substances are e.g. barnase/barstar from *Bacillus amyloliquefaciens* (Hartley, 1988, J. Mol. Biol. 202, 913–915), restriction endonucleases/corresponding methylases such as EcoRI from *E.coli* (Green et al., 1981, J. Biol. Chem. 256, 2143–2153) and EcoRI methylase or similar combinations as described in the review for type II restriction modification systems (Wilson, 1991, Nucl. Acid Res. 19, 2539–2566), bacteriocins and corresponding immunity proteins, e.g. colicin E3/immunity protein from *E. coli* (Lau et al. 1985, Nucl. Acid Res. 12, 8733–8745) or any disruptive substance coding gene which may be neutralized by simultaneous production of antisense RNA under control of promoter-B, such as DNA sequences encoding Diptheria Toxin Chain A (Czako & An, 1991, Plant Physiol. 95, 687–692), RNAses such as RNAse T1, ribonucleases or proteases, ribozymes against mRNA that code for phytotoxic proteins.

According to another aspect of the invention combinations of disrupting and neutralizing substances comprise respectively genes inhibitory to an endogenous gene that encodes a protein or polypeptide product that is essential for cell viability and, as a neutralizing gene, a gene that encodes a protein or polypeptide product capable of substituting the function of the endogenous protein or polypeptide product. Such disruptive genes may be selected from the group consisting of (a) genes encoding ribozymes against an endogenous RNA transcript, (b) genes which when transcribed produce RNA transcripts that are complementary or at least partially complementary to RNA transcripts of endogenous genes that are essential for cell viability, a method known as antisense inhibition of gene expression (disclosed in EP-A 240 208), or (c) genes that when transcribed produce RNA transcripts that are identical or at least very similar to transcripts of endogenous genes that are essential for cell viability, an as yet unknown way of inhibition of gene expression referred to as co-suppression (disclosed by Napoli C. et al., 1990, The Plant Cell 2, 279–289).

According to a preferred embodiment of the invention use is made of antisense genes to inhibit expression of endogenous genes essential for cell viability, which genes are expressed in the nematode feeding structures by virtue of a promoter-A fused upstream to the said antisense gene.

The disruptive effect brought about by the antisense gene inhibitory to the vital endogenous gene is neutralized by the expression of a neutralizing gene-B under the control of a promoter-B according to the invention, said gene-B when expressed produces a protein or polypeptide product which is identical or similar to the protein or polypeptide encoded by the endogenous vital gene and capable of substituting the function of the endogenous gene product in the host plant. It is preferred that the nucleotide sequence of the RNA transcript encoded by the neutralizing gene according to the invention is divergent from the endogenous vital gene RNA transcript to avoid a possible co-suppressive effect. Hence, it is preferred that the neutralizing gene encodes a protein or polypeptide with essentially the same function as the endogenous vital gene, but through an RNA transcript intermediate that is divergent; neutralizing genes which fit this description can be suitably obtained by screening a database for genes obtainable from a different plant species, or even a different non-plant species, such as yeasts, animal eukaryotes or prokaryotes. Preferably, the nucleotide sequence identity of the transcripts encoded by the disruptive antisense transgene and the neutralizing sense transgene is less than 90%, preferably less than 80%, yet more preferably said neutralizing sense transgene encodes a protein or polypeptide gene product that is not identical in amino acid sequence to the disrupted gene product and wherein the nucleotide sequence identity of the transcripts encoded by the neutralizing transgene is less than 75%.

Target genes for antisense disrupter genes are selected from those coding for enzymes that are essential for cell viability, also called housekeeping enzymes, and should be nuclear encoded, preferably as single copy genes, although a small size gene family would also be suitable for the purpose of the invention. Furthermore, the effect of antisense expression of said genes must not be nullified by diffusion or translocation from other cells or organelles of enzyme products normally synthesized by such enzymes. Preferably, genes coding for membrane-translocating enzymes are chosen as these are involved in establishing chemical gradients across organellar membranes. Inhibition of such proteins by antisense expression can not, by definition, be cancelled by diffusion of substrates across the membrane in which these proteins reside. The translocated compound is not limited to organic molecules but can be of inorganic nature; e.g. P, H, OH or electrons.

Preferably, the membrane-translocating enzymes should be present in organelles that increase in numbers during parasitism, thereby illustrating the essential role that such organelles have in cells comprising the NFS. Specific examples for such organelles are mitochondria, endoplasmic reticulum and plasmodesmata (Hussey et al. 1992 Protoplasma 167;55–65, Magnusson & Golinowski 1991 Can. J. Botany 69;44–52). A list of target enzymes is given in Table 1 by way of example but the invention is not limited to the enzymes mentioned in this table. More detailed listings can be assembled from series as Biochemistry of Plants (Eds. Stumpf & Conn, 1988–1991, Vols. 1–16 Academic Press) or Encyclopedia of Plant Physiology (New Series, 1976, Springer-Verlag, Berlin).

Although only in some cases, the genes coding for these enzymes have been isolated and, therefore, the number of gene copies are not known, the criteria that have to be met are described in this invention.

TABLE 1

EXAMPLES OF TARGET ENZYMES FOR ANTISENSE
EXPRESSION IN NFS AND SENSE EXPRESSION OUTSIDE NFS

| enzyme | pathway/organelle |
|---|---|
| ATP synthase | mitochondrion |
| adenine nucleotide translocator | mitochondrion |
| phosphate translocator | mitochondrion |
| tricarboxylate translocator | mitochondrion |
| dicarboxylate translocator | mitochondrion |
| 2-oxo-glutarate translocator | mitochondrion |
| cytochrome C | mitochondrion |
| pyruvate kinase | glycolysis |
| glyceraldehyde-3P-dehydrogenase | glycolysis |
| NADPH-cytochrome P450 reductase | lipid metabolism |
| fatty acid synthase complex | lipid metabolism |
| glycerol-3P-acyltransferase | lipid metabolism |
| hydroxymethyl-glutaryl CoA reductase | mevalonic acid pathway |
| aminoacyl transferase | nucleic acid metabolism |
| transcription factors | nucleic acid metabolism |
| elongation factors | nucleic acid metabolism |

To maximize the antisense effects in a plant host, the use of homologous genes is preferred. With homologous is meant obtainable from the same plant species as the plant host. Heterologous, for the purpose of this specication shall mean obtainable from a different plant or non-plant species. Heterologous shall also comprise synthetic analogs of genes, modified in their mRNA encoding nucleic acid sequence to diverge at least 5% of the host gene. As housekeeping genes are in general highly conserved, heterologous probes from other (plant) species can be used to isolate the corresponding gene from the crop species that is to be made resistant. Such gene isolations are well within reach of those skilled in the art and, in view of the present teaching require no undue experimentation.

To differentiate between possible target genes and select favorable candidates to engineer nematode resistance, the following procedure can be applied by those skilled in the art: via the gene of interest, promoter-sequences can be isolated from genomic DNA and used for cloning in front of a marker gene such as GUS (Jefferson et al. 1987 EMBO J. 6:3901–3907). This expression construct can then be placed in a binary vector suitable for plant transformation, mobilized into Agrobacterium and transferred to the plant genome. Regenerated plants can then be infected with PPN and used for histochemical GUS analysis of entire plants and the feeding structures in particular. In case the used promoter sequence was originally regulating a gene that is essential for nematode development, it should not only be active in large parts of the plant (for it regulates a housekeeping gene) but may be more active inside the feeding structure than in the surrounding tissue. One such example is published by Cramer (1992, Proc. 31st Ann. Meeting Amer. Soc. Nematologists, Vancouver Canada) with the promoter of hydroxy-methyl-glutaryl CoA reductase (HMGR). This promoter becomes more active in infected root tissue, especially those cells involved in feeding the nematode. HMGR is a key (rate-limiting) enzyme for a large number of compounds such as terpenes and sterols. As PPN are unable to synthesize their own sterols (Chitwood & Lusby 1991, Lipids 26;619–627), they are entirely dependent on the plant supply, thus a high HMGR is advantagous to the parasitizing nematode. Vice versa, down-regulation of this enzyme through antisense expression in feeding cells, as in the description of the present invention, will have severe effects on the development of the nematode.

Alternatively, for the selection of favorable candidates, the availability of mutants in unicellular eukaryotes such as yeast or Chlamydomonas can be used as indication. If for a particular enzyme, a large number of mutants are available then it is likely that this enzyme is redundant, present as multicopy gene families, or that alternative pathways are available to circumvent the mutated enzyme (Strathern, Jones & Broach (Eds.) 1981 The molecular biology of the yeast *Saccharomyces cerevisiae*. Cold Spring Harbor Laboratory Press, New York). Such genes are less suitable for the methods described in this invention. By contrast, mutations in enzymes that are usually lethal for the recipient cell and therefor rarely available, indicate that an antisense deregulation of such genes will inhibit the proper development of that cell and can be used for the approach to engineer reduced susceptibility to PPN as desclosed in this invention. Gene disruption methods are available to test if a gene is essential for cell viability in which case the disruption event will lethal (Rothstein, 1983 Methods Enzym. 101; 202–211). The homologous gene can then be isolated from the target crop with the yeast gene as a probe.

The application of this invention is not restricted to the plant species that are shown by way of demonstration. The choice of the plant species is primarily determined by the amount of damage through PPN infections estimated to occur in agriculture and the amenability of the plant species to transformation. Plant genera which are damaged during agricultural practice by PPN and which can be made significantly less susceptible to PPN by ways of the present invention include but are not limited to the genera mentioned in Table 2.

Nematode species as defined in the context of the present invention belong to the superfamily Heteroderoidea and are divided among the families Heteroderidae and Meloidogynidae and include, but are not limited to the species mentioned in Table 2.

A suitable promoter-A is defined as a promoter that drives expression of a downstream gene inside the NFS, at levels sufficient to be detrimental to the metabolism and/or functioning and/or viability of the NFS, while this promoter should preferably, but not necessarily, be inactive in tissues outside the NFS; it should at least never be active outside NFS at such levels that the activity of the disruptive substance, encoded by gene-A, can not be neutralized sufficiently by products from gene-B.

A suitable promoter-A can be identified through screening of plants, expressing gene-B under the control of a suitable promoter-B, said plants having regenerated after a second round of transformation with a recombinant DNA construct carrying promoterless gene-A constructs and preferably a second selectable marker (different from the one on the promoter-B/gene-B construct) and analyzing said plants for reduced susceptibility to PPN. Random integration of the promoterless gene-A construct in regions with promoter activity will allow, after infection with PPN of the transformed regenerants, the selection of plants with sufficient gene-A expression in the NFS while maintaining a normal phenotype in all other plant parts as a result of the neutralizing effect of gene-B in tissues outside the NFS. As shown by our experiments there is in principle no need to isolate a promoter-A with properties as described in this invention since the integration procedure works with a relatively high frequency.

This method, as illustrated in a different context by Kertbundit et al., 1991, Proc. Nat. Acad. Sci. USA 88, 5212–5216, is especially suitable with Arabidopsis plants because the small genome yields a relatively high frequency of integration in transcriptionally active regions of the genome.

Alternatively, a suitable promoter-A can be isolated via genes that are expressed at increased levels inside the NFS during nematode infection. Such genes can be isolated through differential screening of cDNA clones made from mRNA extracted from infected and healthy roots as was demonstrated for potato (Gurr S. J. et al. 1991, Mol. Gen. Genet. 226, 361–366). Although such promoters have never been described in detail, they can be selected and isolated in a well known manner from a plant by:

1. searching for a mRNA which is present primarily (although not necessarily exclusively) in infected root tissue,
2. isolating this mRNA
3. preparing a cDNA from this mRNA
4. using this cDNA as a probe to identify the regions in the plant genome which contain DNA coding for this specific mRNA
5. identifying and isolating the upstream (5') sequences from the DNA coding for this specific mRNA and that contains the promoter region.

Preferably, the infected roots used for mRNA isolation should be enriched for NFS e.g. by synchronous infection (Hammond-Kosack et al. 1989 Physiol. Mol. Plant. Pathol. 35, 495–506) or through direct isolation of feeding structures from plants in which NFS are visible at low magnification. For example feeding-structures that develop inside Arabidopsis roots can be seen at low magnification and are easy to isolate with a minimum of contaminating cells (Sijmons et al. 1991, Plant J. 1, 245–254). This allows the isolation, preferably using molecular enrichment procedures (Dickinson et al., 1991 Adv. Mol. Gen. Plant-Microbe Interact. 1 276–279) of genes corresponding to these RNA's and subsequent isolation of upstream promoter elements. Once identified, similar genes can be isolated from other plant species when the identified gene is used as a probe as in step 4. Species-specific upstream sequences can then be isolated from these other plant species for use in a similar strategy as described in this invention. Upstream sequences of identified genomic clones can be fused to a gene-A for insertion in a suitable expression vector for plant transformation such as pMOG22 or pMOG23.

Alternatively, suitable promoters for expression of gene-A can be isolated via interposon tagging (Topping et al., 1991, Developm. 112, 1009–1019). In this approach, a number of different transgenic plants are regenerated after transformation with T-DNA from Agrobacterium carrying promoterless GUS constructs such as described by Topping et al. (1991, Developm. 112, 1009–1019) or pMOG452 as described in the Examples. After infection with a root-knot or cyst nematode and allowing some development of the NFS, roots can be stained for GUS activity. The random integration of the T-DNA enables the identification of promoter sequences that are active primarily in the NFS or are e.g. root-specific but remain active inside the NFS. This type of interposon tagging of promoter sequences is especially well established in Arabidopsis (Kertbundit et al., 1991, Proc. Nat. Acad. Sci. USA 88, 5212–5216) and tobacco (Topping et al., 1991, Developm. 112, 1009–1019). The 5' upstream sequences responsible for GUS expression can be isolated with inverted polymerase chain reaction (inverted PCR) (Does et al. 1991, Plant Mol. Biol. 17, 151–153). Once suitable regulatory sequences are identified or genes that are transcribed inside NFS, they can be used as probes for the isolation of homologous sequences from other plant species. In turn, these sequences from other species can be fused to a gene-A for insertion in a suitable vector for plant transformation. Alternatively, a suitable promoter-A is made from a truncated version of the rolc-promoter derived from the nucleotide sequence 11286 up to 12132 between the open reading frames 11 and 12 of the TL-DNA from an *Agrobacterium rhizogenes* plasmid pRiA4 (Slightom et al. 1986, J. Biol. Chem. 261, 108–121). Similarly, promoters identified through the above described interposon tagging technique that show specificity for root vascular tissue but are suppressed during NFS development, can be made insensitive to NFS suppression by removing those parts of the promoter that are responsible for the down-regulation as is shown with the truncated version of the rolc promoter. Such mutated promoter sequences then become suitable for use as promoter-A.

Alternatively, the following promoter sequence can be used as promoter-A; a truncated version of a tobacco root-specific promoter Δ0.3TobRB7 (Yamamoto et al. 1991 Plant Cell 3; 371–382). The full length sequence of the TobRB7 promoter is highly active inside NFS and this activity becomes more specific for the NFS when the truncated Δ0.3 version of the promoter is used (Taylor et al. 1992, Proc. 31st Ann. Meeting Amer. Soc. Nematologists, Vancouver Canada).

Alternatively, promoters that are active in root vascular tissue or other plant parts and become more active specifically in the NFS (e.g. hydroxy-methyl-glutaryl CoA reductase promoter; Cramer 1992, Proc. 31st Ann. Meeting Amer. Soc. Nematologists, Vancouver Canada) can also be used as promoter-A, as long as the activity outside the NFS is never higher than the activity of promoter-B.

A suitable promoter-B is defined as a promoter that drives expression in substantially all cells wherein gene-A is expressed, with the proviso that it does not drive expression inside a nematode feeding structure, or not effectively. (With 'substantially all cells' is meant at least those cells that should be viable in order to get normal plant growth and or development required for commercial exploitation of such plants. (As an illustration of plants in which the disruptive effect is not neutralized in exactly all cells of the host plant and which are nevertheless viable and suitable for commercial exploitation, are those which express a disrupter gene according to this invention in stamen cells; this may yield male-sterile plants, which is even regarded as a commercially attractive trait in some crops). Promoter sequences are regulatory sequences active in directing transcription in plants and can be obtained from plants or plant viruses, or may be chemically synthesized. The regulatory sequences may also include enhancer sequences, such as found in the 35S promoter of CaMV (Kay et al., 1987, Science 236, 1299–1302), and mRNA stabilizing sequences such as the leader sequence of Alfalfa Mosaic Virus RNA4 (Brederode et al., 1980, Nucl. Acids Res. 8, 2213–2223) or any other sequences functioning in a like manner.

Alternatively, to provide for expression in all or effectively all plant tissues, a promoter-B/gene-B can be complemented with a second promoter-B'/gene-B having a expression pattern complementary to promoter-B/gene-B, with the proviso that neither promoter-B nor promoter-B' drives expression in the NFS. Also hybrid promoters, comprising (parts of) different promoters combined as to provide for the required expression pattern as defined herein, fall within the scope of the present invention.

Preferebly, promoter-B is the Cauliflower Mosaic Virus 35S promoter or derivatives thereof, which is generally considered to be a strong constitutive promoter in plant tissues (Odell et al. 1985 Nature 313, 810–812). Another preferred example for promoter-B is the strong root promoter rolD (Leach & Aoyagi 1991 Plant Sci. 79; 69–76) from plasmid pRiA4 of *Agrobacterium rhizogenes*; the 5' flanking region of ORF15 (Slightom et al. 1986, J. Biol. Chem. 261, 108–121). The suitability of other constitutive promoters such as the nopaline synthase promoter (Bevan, 1984, Nucl. Acids Res. 12, 8711–8721) or figwort mosaic virus promoter (EP-A 426 641) for use as promoter-B can be tested through fusion to marker genes such as GUS (Jefferson, 1987, Plant Mol. Biol. Reporter 5, 387–405), transfer of these constructs to plants and histochemical analysis of such transgenic plants after infection with PPN.

Other regulatory sequences such as terminator sequences and polyadenylation signals include any such sequence functioning as such in plants, the choice of which is within the level of skill of the average skilled person in the art. An example of such sequences is the 3' flanking region of the nopaline synthase (nos) gene of *Agrobacterium tumefaciens* (Bevan, 1984, Nucl. Acids Res. 12, 8711–8721).

According to another embodiment of the invention a method is provided for reducing damage to crops by plant parasitic nematodes, which comprises growing plants that contain a herbicide resistance gene placed under the control of a promoter-B that is expressed at least in the roots of the plants, but not effectively in the nematode feeding structure, comprising the steps of 1) growing the said plants,
2) contacting the roots of said plants with a herbicide. For this embodiment of the invention, the requirements for expression of gene-B, are more strict, i.e. it must be expressed in all cells that are contacted with the herbicide, except the NFS. For this purpose, promoter-B can be complemented with a second constitutive promoter-B' (linked to another or the same copy of gene-B) provided that promoter-B' is also not expressed in the NFS. Suitable examples for this embodiment of the invention include, but are not limited to herbicides e.g. the class of compounds named sulfonylureas (Mazur & Falco, 1989, Ann. Rev. Plant Physiol. 40, 441–470). The example used in this invention (hygromycin resistance gene under control of 35S promoter and subsequent growth and infection in hygromycin-containing medium) is merely to demonstrate the feasibility of this approach. The choice of the herbicide for agricultural use is primarily determined by the availability of a herbicide resistance gene, the cost and environmental effects of the herbicide, its suitability for formulation, either for soil injection or for spraying, the mobility in soil and the ability to reach and affect cells comprising the NFS, the mobility in plant tissues and the ability to reach NFS cells when sprayed above soil.

As several nematode species show a wide host range and can parasitize on a large number of different plant species, and also because the feeding structures in different plant species show a high degree of similarity, it is expected that the down-regulation (i.e. absence of activity) of promoters such as CaMV 35S or other promoters that fit the description of a constitutive promoter as described in this invention will occur in a wide range of plant species besides the examples shown in this invention. The invention is not limited to the species that are shown by way of demonstration. The choice of the plant species is primarily determined by the amount of damage through PPN infections estimated to occur in agriculture and the amenability of the plant species to transformation. Plant genera which are damaged during agricultural practice by PPN and which can be made significantly less susceptible to PPN by ways of the present invention include but are not limited to the genera mentioned in Table 2.

Nematode species as defined in the context of the present invention include all plant-parasitic nematodes that modify host cells into specially adapted feeding structures which range from migratory ectoparasites (e.g. Xiphinema spp.) to the more evolved sedentary endoparasites (e.g. Heteroderidae, Meloidogynae or Rotylenchulinae). A list of parasitic nematodes are given in Table 2, but the invention is not limited to the species mentioned in this table. More detailed listings are presented in Zuckerman et al. (eds., in: Plant Parasitic Nematodes, Vol. I 1971, New York, pp. 139–162).

The methods according to the invention to combat damage to crops due to nematode invasion is likewise applicable with non-nematode pests and pathogens, whenever said pathogen or pest locally down-regulates plant promoters at the site of infestation (e.g. in fungi-induced haustoria or aphid-induced galling). The principle of effecting the production of a neutralizing substance in all or most of the non-infestated plant parts to neutralize a cell disruptive substance the production of which is effected in at least the site of infestation, is independent of the type or species of the pathogen or pest.

TABLE 2

EXAMPLES OF PLANT-PARASITIC NEMATODES AND THEIR PRINCIPAL HOST PLANTS

| Nematode Species | Principal Host Plants |
| --- | --- |
| Meloidogyne | |
| M. hapla | wide range |
| M. incognita | wide range |
| M. exigua | coffee, tea, Capsicum, Citrullus |
| M. indica | Citrus |
| M. javanica | wide range |
| M. africana | coffee |
| M. graminis | cereals, grasses |
| M. graminicola | rice |
| M. arenaria | wide range |
| Heterodera & Globodera | |
| H. mexicana | Lycopersicon esculentum, Solanum spp. |
| H. punctata | cereals, grasses |
| G. rostochiensis | Solanum tuberosum, Solanum spp, Lycopersicon esculentum |
| G. pallida | Solanum tuberosum |
| G. tabacum | Nicotiana tabacum, Nicotiana spp. |
| H. cajani | Cajanus cajan, Vigna sinensis |
| H. glycines | Glycine max, Glycine spp. |
| H. oryzae | Oryza sativa |
| H. schachtii | Beta spp, Brassica spp, |
| H. trifolii | Trifolium spp. |
| H. avenae | cereals, grasses |
| H. carotae | Daucus carota |
| H. cruciferae | Cruciferae |
| H. goettingiana | Pisum sativum, Vicia spp. |

Within the context of this invention, a plant is said to show reduced susceptibility to PPN if a statistically significant decrease in the number of mature females developing at the surface of plant roots can be observed as compared to control plants. Susceptible/resistance classification according to the number of maturing females is standard practice both for cyst- and root-knot nematodes (e.g. LaMondia, 1991, Plant Disease 75, 453–454; Omwega et al., 1990, Phytopathol. 80, 745–748).

The basic principle of reducing the plant's susceptibility to plant parasitic nematodes according to the invention is the manipulation of the nematode feeding structure. Manipulation of the nematode feeding structure for the purpose of this description of the invention shall include both preventing or retarding NFS formation as well as disruption once formation of the NFS is in an advanced stage.

It is preferred to prevent or retard formation of the NFS, i.e. during the first stages of nematode invasion; to that end the NFS disruptive gene-A must be under the control of a promoter-A that drives expression at the onset of NFS formation.

However, in principle, it will also be acceptable if a disruptive gene-A is under the control of a promoter-A that drives expression of the disrupter gene-A in a more advanced stage of NFS formation causing the NFS to decline or to collapse. Either of these two extremes will provide the infected plant with decreased susceptibility towards the invading nematode. For the purpose of this invention the expression "disruption of the NFS" shall include retardation of NFS formation, decline of NFS formation once formed, or in the process of being formed, as well as total collapse of the NFS formed.

Reduced susceptibility to a plant parasitic nematode may be the result of a reduction of the number of NFS of the infected plant root, a reduction in the advancement of NFS formation, or a combination of both effects.

A nematode feeding structure according to the present invention shall include an initial feeding cell, which shall mean the cell or a very limited number of cells destined to become a nematode feeding structure, upon induction of the invading nematode.

A NFS disruptive effect according to the invention is not limited to adverse effects on the NFS only; also disruptive effects are contemplated that in addition have an adverse effect on nematode development by way of direct interaction.

Several techniques are available for the introduction of recombinant DNA containing the DNA sequences as described in the present invention into plant hosts. Such techniques include but are not limited to transformation of protoplasts using the calcium/polyethylene glycol method, electroporation and microinjection or (coated) particle bombardment (Potrykus, 1990, Bio/Technol. 8, 535–542).

In addition to these so-called direct DNA transformation methods, transformation systems involving vectors are widely available, such as viral vectors (e.g. from the Cauliflower Mosaic Virus (CaMV) and bacterial vectors (e.g. from the genus Agrobacterium) (Potrykus, 1990, Bio/Technol. 8, 535–542). After selection and/or screening, the protoplasts, cells or plant parts that have been transformed can be regenerated into whole plants, using methods known in the art (Horsch et al., 1985, Science 225, 1229–1231). The choice of the transformation and/or regeneration techniques is not critical for this invention.

According to a preferred embodiment of the present invention use is made of so-called binary vector system (disclosed in EP-A 120 516) in which Agrobacterium strains are used which contain a helper plasmid with the virulence genes and a compatible plasmid, the binary vector, containing the gene construct to be transferred. This vector can replicate in both *E.coli* and in Agrobacterium; the one used here is derived from the binary vector Bin19 (Bevan, 1984, Nucl. Acids Res. 12, 8711–8721). The binary vectors as used in this example contain between the left- and right-border sequences of the T-DNA, an identical NPTII-gene coding for kanamycin resistance (Bevan, 1984, Nucl. Acids Res. 12, 8711–8721) and a multiple cloning site to clone in the required gene constructs.

The transformation and regeneration of monocotyledonous crops is not a standard procedure. However, recent scientific progress shows that in principle monocots are amenable to transformation and that fertile transgenic plants can be regenerated from transformed cells. The development of reproducible tissue culture systems for these crops, together with the powerful methods for introduction of genetic material into plant cells has facilitated transformation. Presently, preferred methods for transformation of monocots are microprojectile bombardment of explants or suspension cells, and direct DNA uptake or electroporation (Shimamoto, et al, 1989, Nature 338, 274–276). Transgenic maize plants have been obtained by introducing the *Streptomyces hygroscopicus* bar gene, which encodes phosphinothricin acetyltransferase (an enzyme which inactivates the herbicide phosphinothricin), into embryogenic cells of a maize suspension culture by microparticle bombardment (Gordon-Kamm, 1990, Plant Cell, 2, 603–618). The introduction of genetic material into aleurone protoplasts of other monocot crops such as wheat and barley has been reported (Lee, 1989, Plant Mol. Biol. 13, 21–30). Wheat plants have been regenerated from embryogenic suspension culture by selection only the aged compact and nodular embryogenic callus tissues for the establishment of the embryogenic suspension cultures (Vasil, 1990 Bio/Technol. 8, 429–434). The combination with transformation systems for these crops enables the application of the present invention to monocots. These methods may also be applied for the transformation and regeneration of dicots.

The following examples are given only for purposes of illustration and do not intend to limit the scope of the invention. Unless otherwise stated in the Examples, all procedures for manipulating recombinant DNA were carried out by using standard procedures as described in Sambrook et al. (Molecular Cloning, A laboratory Manual 2nd Edition, Cold spring Harbor Laboratory (1990).

Example I

Construction of Intermediate Vectors a) Construction of pMOG18

A detailed description for the construction of the expression vector pMOG18 is given in Pen et al. (1991) Eur. Pat. Appl. 0 449 375 A2. This construct the Cauliflower Mosaic Virus (CaMV) 35S promoter with a double enhancer sequence, the leader sequence of RNA4 from Alfalfa Mosaic Virus (AlMV), the gene encoding β-glucuronidase (originating from plasmid pRAJ275; (Jefferson, 1987, Plant Mol. Biol. Reporter 5, 387–405) followed by the nopaline synthase (nos) transcription terminator. The entire expression construct is present as an EcoRI/HindIII fragment in pMOG18.

b) Construction of pMOG180

The expression vector pMOG180 is a derivative of pMOG18 wherein the gene coding for GUS is removed; other genes can be inserted between the AlMV RNA4 leader and 3' nos terminator as a BamHI fragment.

For this purpose, the EcoRI/NcoI fragment from pMOG18, containing the 35S promoter and AlMV RNA4 leader sequences is synthesized by PCR amplification using as primer sets 5' GTTTCTACAGGACGGAGGATCCTG-GAAGTATTTGAAAGA 3' (SEQIDNO:1) and 5' CAGC-TATGACCATGATTACG 3' (SEQIDNO:2) thus mutating the NcoI site into a BamHI site. pMOG18 vector is then cut with EcoRI and BamHI after which the newly synthesized EcoRI/BamHI fragment is ligated between these restriction sites. To circumvent PCR-induced random mutations in the promoter sequences, the EcoRI/EcoRV fragment in the PCR synthesized EcoRI/BamHI fragment is replaced by wildtype sequences from pMOG18. The short EcoRV/BamHI fragment is checked for mutations by sequencing. The resulting expression vector is plasmid pMOG180.

c) Construction of pMOG707

Figure 2:
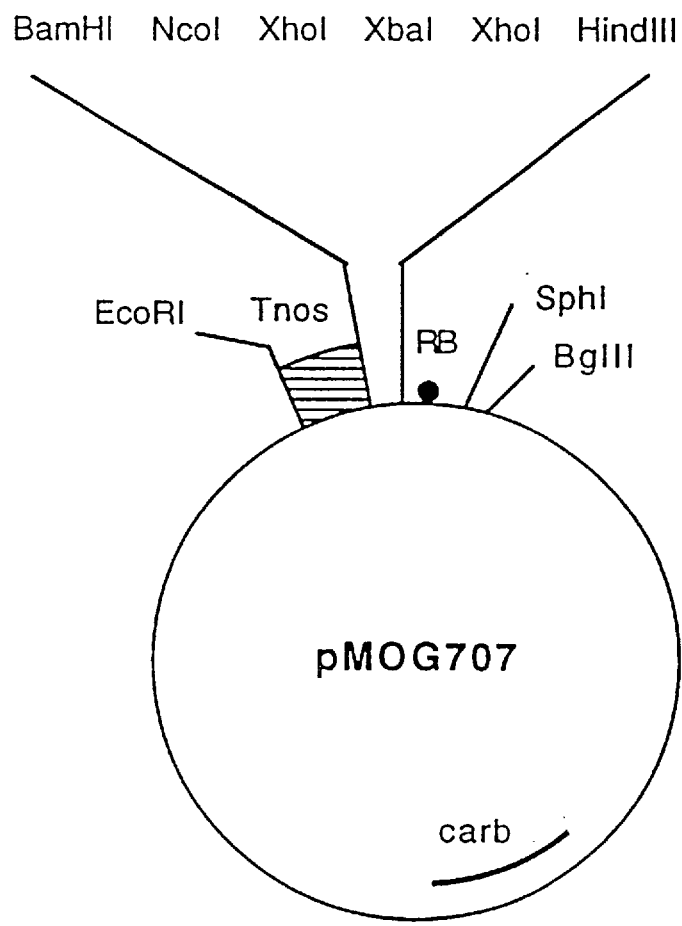
FIG. 2. Plasmid pMOG707, intermediate vector constructed for cloning purposes.

A cloning vector pMOG707 is constructed, containing a right border T-DNA sequence, a multiple cloning site and a terminator for the purpose of cloning different promoter/ gene combinations on a suitable fragment. This vector is constructed in the following manner: in the cloning vector pMTL26 (Chambers et al. 1988 Gene 68, 139–149) the XhoI site is removed by XhoI digestion, blunt-ended with Klenow polymerase followed by religation, resulting in pMTL26/2. This modified PMTL vector is used to clone the EcoRI-BqlII fragment from pMOG23, containing the multiple cloning site and the right border sequences, resulting in pMOG584bis. The polylinker sequence is extended by inserting a synthetic linker between the BamHI and XhoI site, thus creating additional NcoI, XhoI and XbaI sites. Subsequently, the nopaline synthase transcription terminator is isolated as a BamHI/HindIII fragment from the plasmid ROK1 (Baulcombe et al. 1986, Nature 321;446), ligated to a synthetic adaptor such that the HindIII site is not recovered and an EcoRI site is introduced and subsequently cloned into the extended pMOG584bis as a BamHI-EcoRI fragment, resulting in plasmid pMOG707 (FIG. 2).

Example II

Construction of Agrobacterium strain MOG101

A binary vector system was used to transfer gene constructs into Arabidopsis plants. The helper plasmid containing the *Agrobacterium tumefaciens* virulence functions was derived from the octopine Ti-plasmid pTiB6. MOG101 is a *Agrobacterium tumefaciens* strain carrying a non-oncogenic Ti-plasmid from which the entire T-region was deleted and substituted by a bacterial Spectinomycin resistance marker from transpososn Tn 1831 (Hooykaas et al., 1980 Plasmid 4, 64–75).

Figure 3:
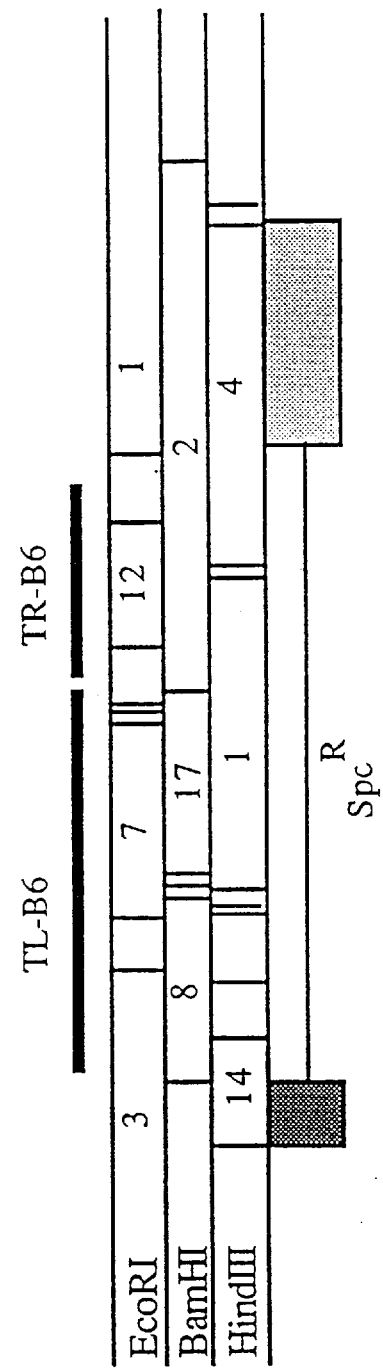
FIG. 3. Restriction map of fragment from Ti-plasmid pTiB6
Figure 4:
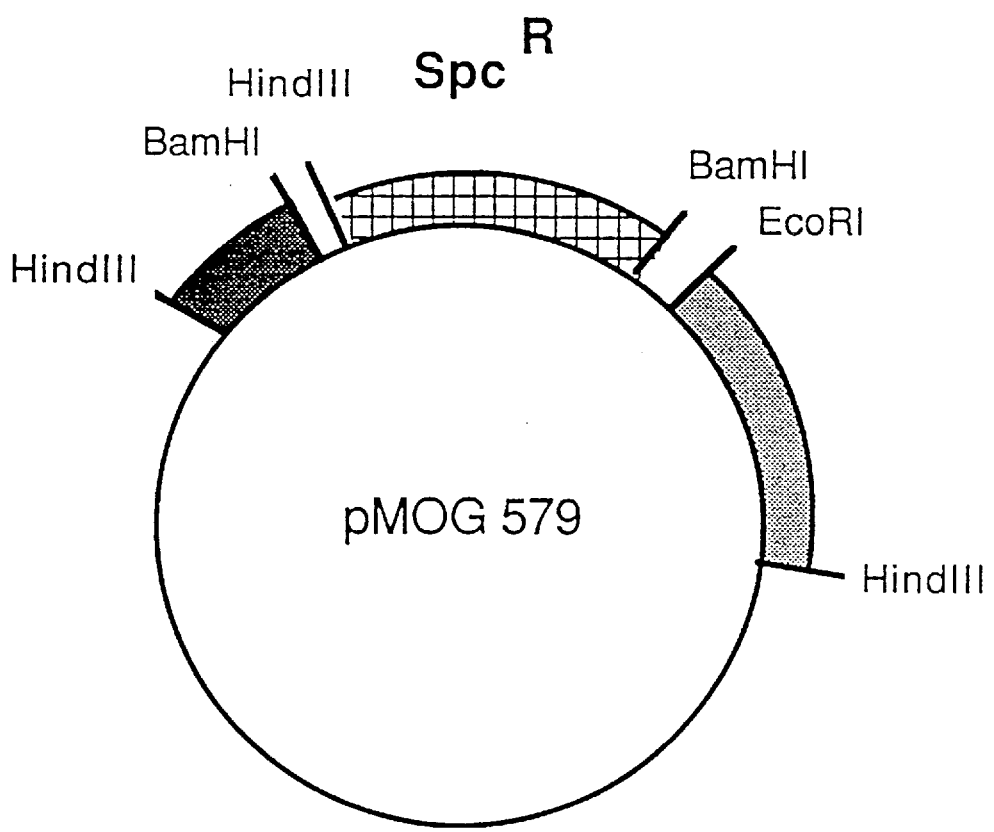
FIG. 4. Intermediate vector pMOG579

The Ti-plasmid pTiB6 contains two adjacent T-regions, TL (T-left) and TR (T-right). To obtain a derivative lacking the TL- and TR-regions, we constructed intermediate vector pMOG579. Plasmid pMOG579 is a pBR322 derivative, which contains the 2 Ti-plasmid fragments that are located to the left and right, outside the T-regions (FIG. 3). The 2 fragments (shown in dark) are separated in pMOG579 (FIG. 4) by a 2.5 kb BamHI-HindIII fragment from transposon Tn1831 (Hooykaas et al., 1980 Plasmid 4, 64–75) carrying the spectinomycin resistance marker (FIG. 4). The plasmid was introduced into *Agrobacterium tumefaciens* strain LBA1010 [C58-C9 (pTiB6)=a cured C58 strain in which pTiB6 was introduced (Koekman et al. 1982, Plasmid 7, 119–132)], by triparental mating from *E.coli*, using HB101 containing pRK2013 as a helper. Transconjugants were selected for resistance to Rifampicin (20 mg/l) and spectinomycin (250 mg/l). A double recombination between pMOG579 and pTiB6 resulted in loss of carbenicillin resistance (the pBR322 marker) and deletion of the entire T-region. Of 5000 spectinomycin resistant transconjugants replica plated onto carbenicillin (100 mg/l) containg medium, 2 were found sensitive. Southern analysis showed that a double crossing over event had deleted the entire T-region (not shown). The resulting strain was called MOG101. This strain and its construction is analogous to strain GV2260 (Deblaere et al. 1985, Nucl. Acids Res. 13, 4777–4788).

Example III

Construction of binary vectors
a) Construction of pMOG23
In this example the construction of the binary vector pMOG23 (in *E. coli* K-12 strain DH5alpha, deposited at the Centraal Bureau voor Schimmel-cultures on Jan. 29, 1990 under accession number CBS 102.90) is described.

The binary vector pMOG23 is a derivative of vector Bin19 (Bevan, 1984, Nucl. Acids Res. 12, 8711–8721). To obtain pMOG23, the vector Bin19 is changed in a way not essential for the present invention, using techniques familiar to those skilled in the art of molecular biology.

Figure 5:
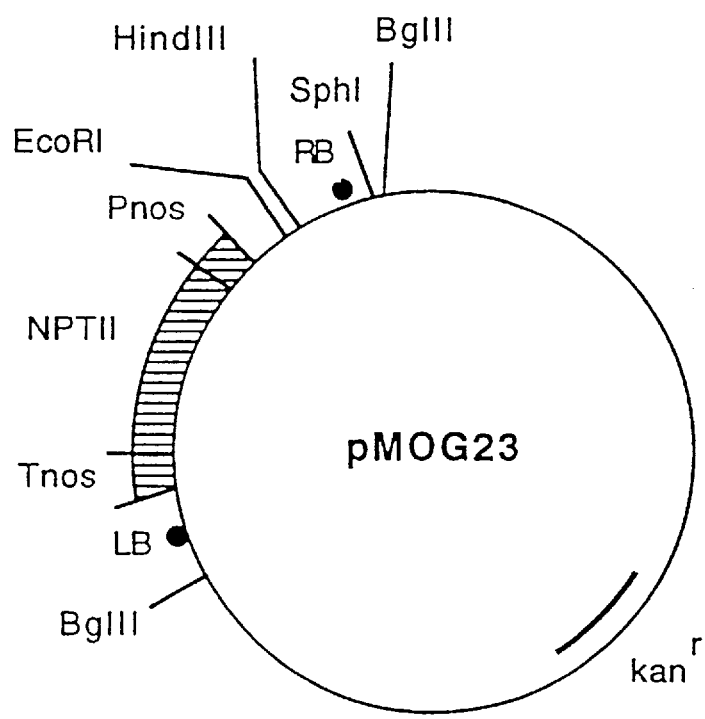
FIG. 5. Binary vector pMOG23

First, the positions of the left border (LB) and the right border (RB) are switched with reference to the neomycine phosphotransferase gene II (NPTII gene). Secondly, the orientation of the NPTII gene is reversed giving transcription in the direction of LB. Finally the polylinker of Bin19 is replaced by a polylinker with the following restriction enzyme recognition sites: EcoRI, SmaI, BamHI, XbaI, SacI, XhoI and HindIII (FIG. 5).
b) Construction of pMOG22

Figure 6:
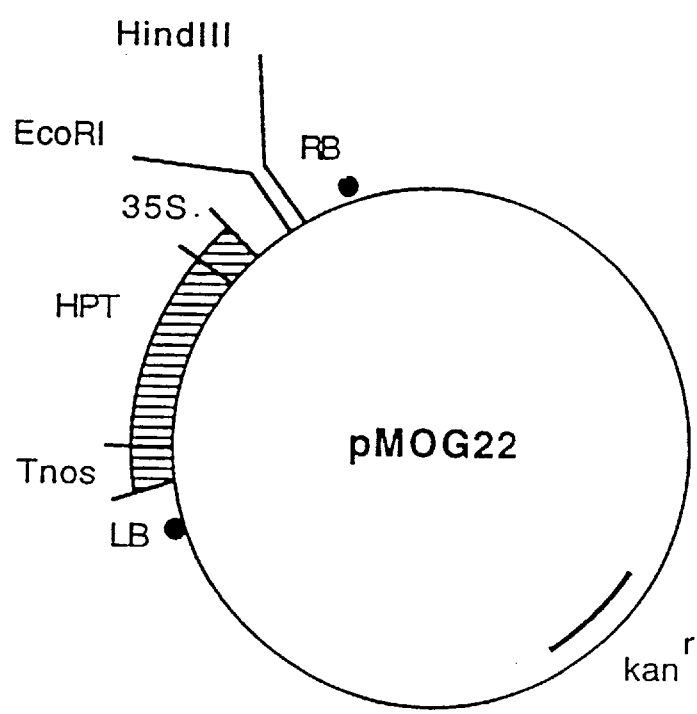
FIG. 6. Binary vector pMOG22

The binary vector pMOG22 is a derivative of pMOG23 wherein the NPTII gene is replaced with a hygromycin resistance gene (HPT, hygromycin phosphotransferase, taken from plasmid PLG90; Van den Elzen et al., 1985, Plant Mol. Biol. 5, 299–302) using techniques familiar to those skilled in the art of molecular biology. pMOG22 construction is described in detail in Cornelissen et al. (1991, Eur. Pat. Appl. 0 440 304 A1) and is deposited in *E. coli* K-12 strain DH5alpha at the Centraal Bureau voor Schimmel-cultures on Jan. 29, 1990 under accession number CBS 101.90 (FIG. 6).
c) Construction of pMOG25 & pMOG28; binary vectors containing the 35S promoter and the GUS gene.

Figure 7:
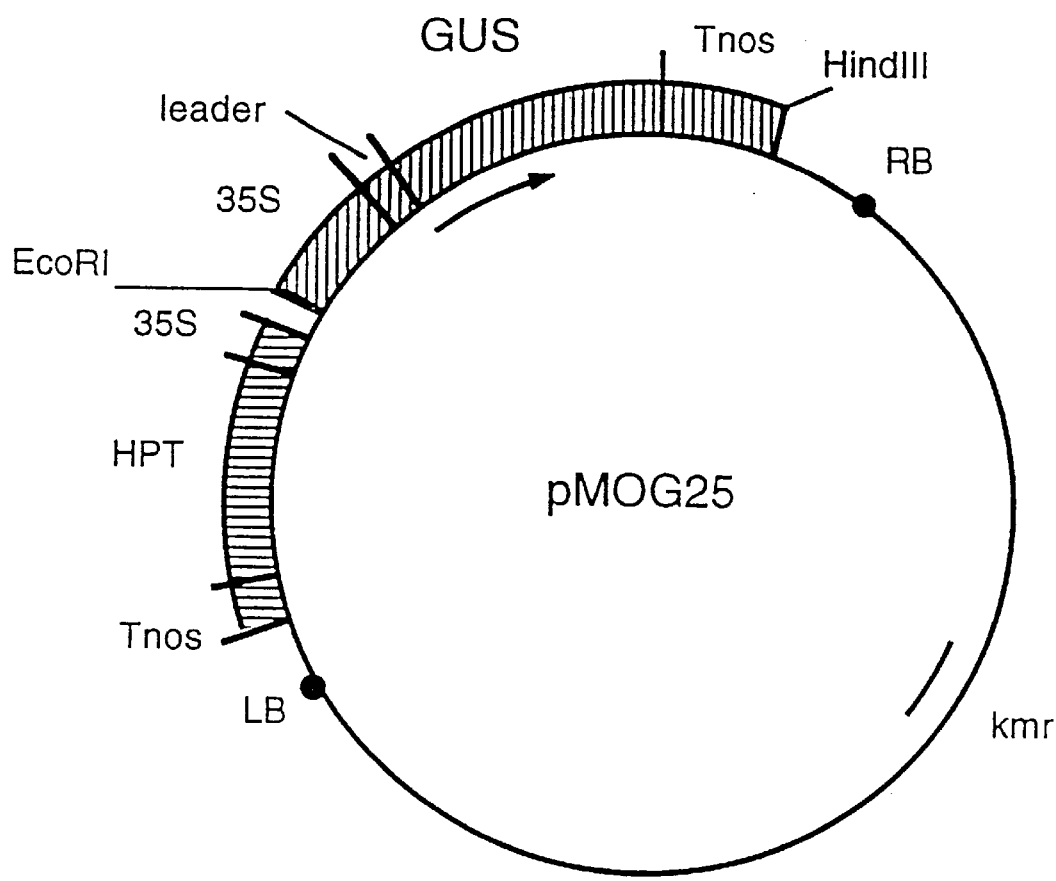
FIG. 7. Binary vector pMOG25. Plasmid containing 35S-HPT and 35S-GUS between left and right border of the T-DNA.

The EcoRI/HindIII fragment from pMOG18 is cloned into the polylinker of pMOG22 and pMOG23, resulting in binary plasmids pMOG25 (FIG. 7) and pMOG28 respectively.
d) Construction of pMOG452; a binary vector containing a promoterless GUS gene The gene coding for GUS fused to a 3'nos terminator sequence but without any 5' regulatory promoter sequences was cloned as a EcoRI-BamHI fragment from pBI101 plasmid (Jefferson, 1987, Plant Mol. Biol. Reporter 5, 387–405) into the multiple cloning site of binary vector pMOG23, resulting in binary plasmid pMOG452 (FIG. 8).
e) Construction of pMOG630; a binary vector containing the rolD promoter and the GUS gene.

Figure 8:
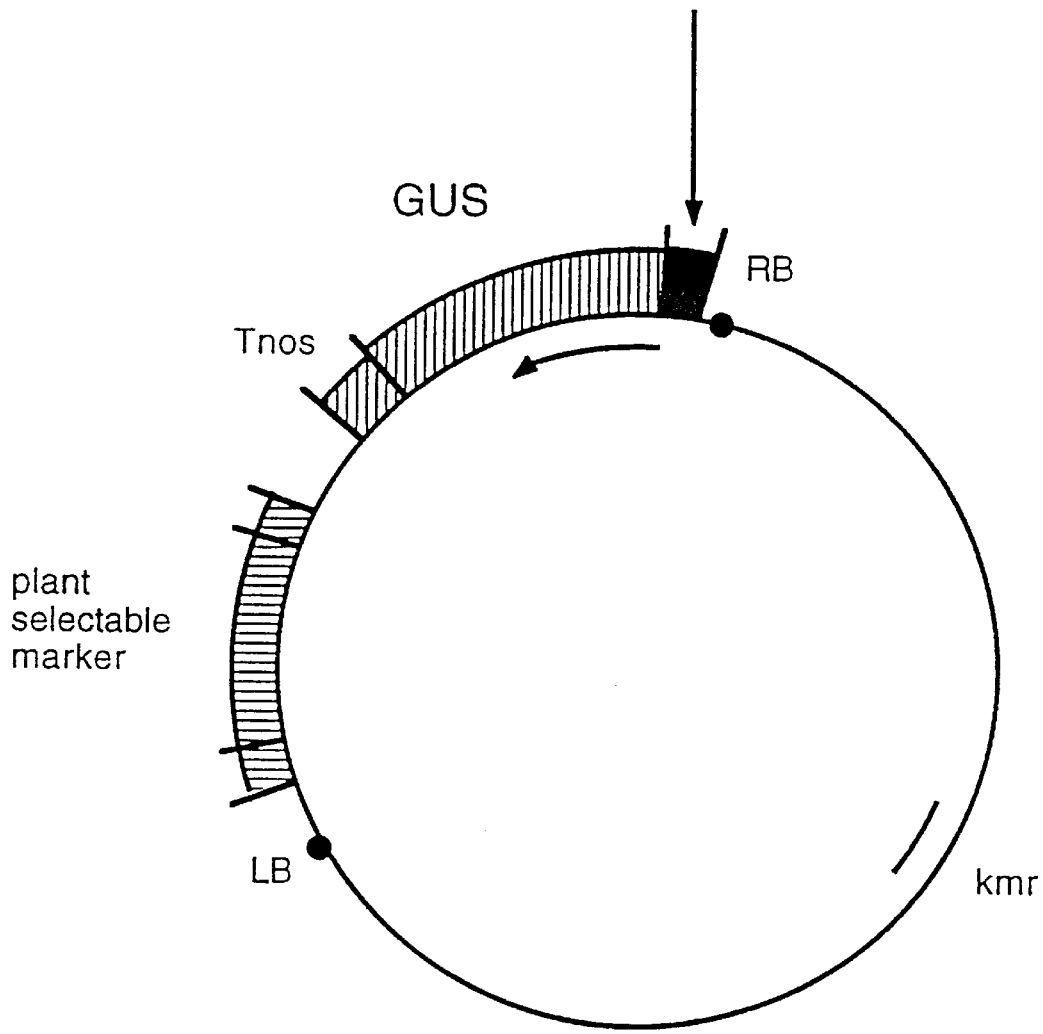
FIG. 8. Binary vectors pMOG452, pMOG630 & pMOG679. These plasmid are derivatives of pMOG23 or pMOG22 and contain either a promoterless GUS construct, a rolD-promoter/GUS construct or truncated rolC-promoter/ GUS construct and a plant selectable marker (NPTII or HPT).
Figure 9:
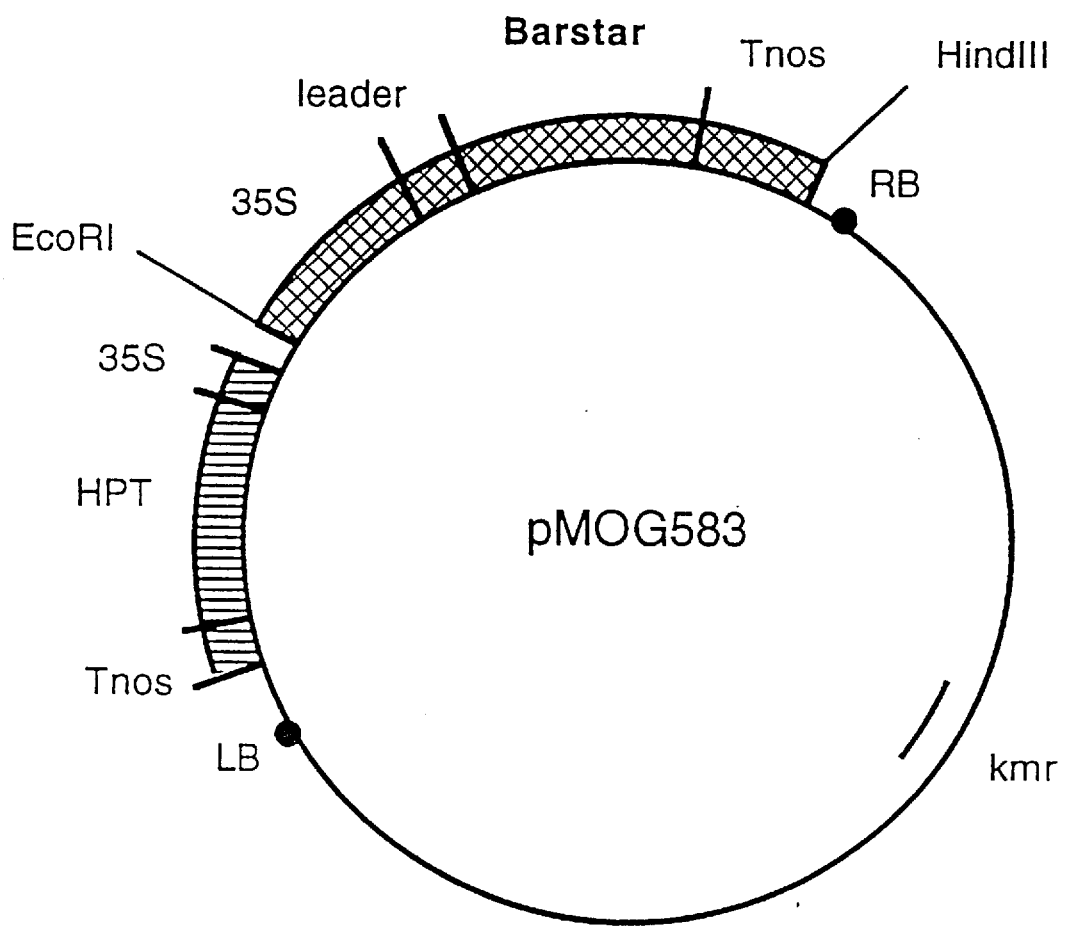
FIG. 9. Binary vector pMOG583. This plasmid is a derivative of pMOG22 and contains a 35S-promoter fused to a Barstar gene.
Figure 10:
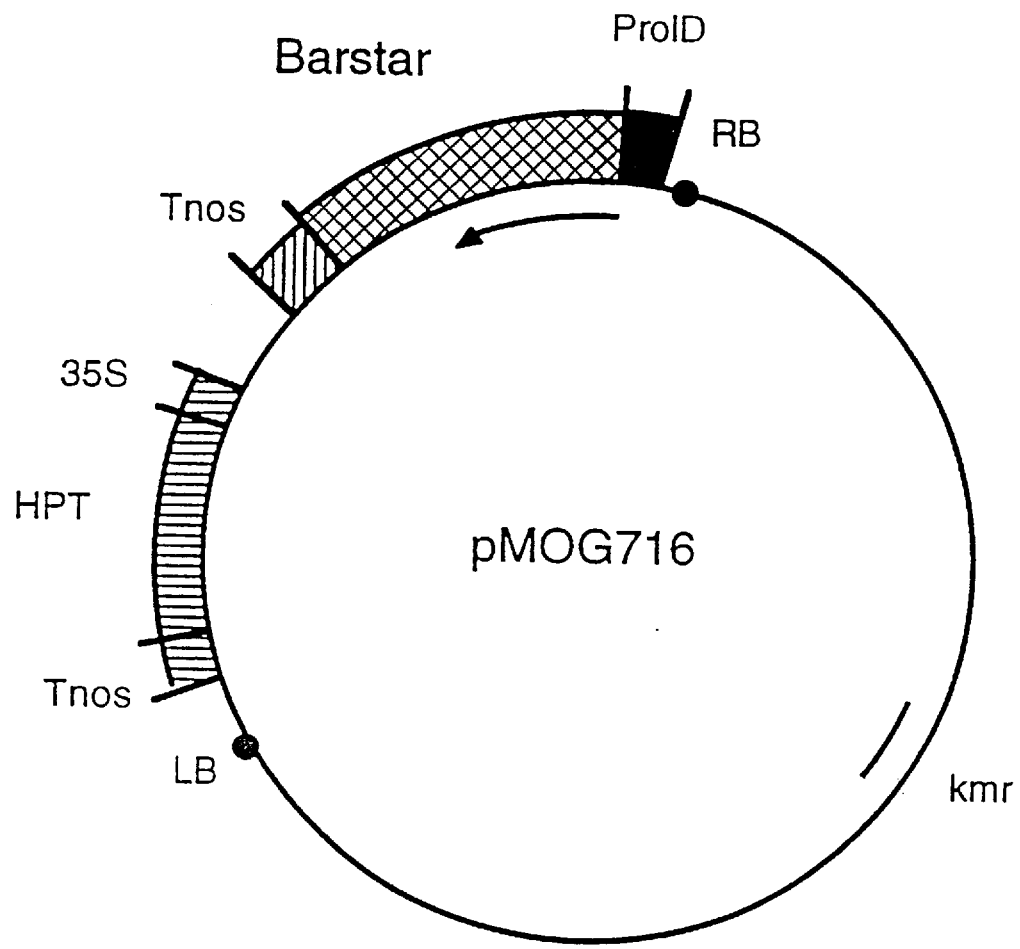
FIG. 10. Binary vector pMOG716. This plasmid is a derivative of pMOG22 and contains a rolD-promoter fused to a Barstar gene.

The 373 bp 5' flanking region of rolD of plasmid pRiA4 (Leach & Aoyagi 1991, Plant Sci. 79, 69–76) is cloned in front of the GUS gene of plasmid pMOG452 using standard cloning techniques, resulting in binary plasmid pMOG630 (FIG. 8). Very similar constructs for analysis of rolD promoter activity are described in.
f) Construction of pMOG679; a binary vector containing a truncated rolC promoter and the GUS gene A truncated version of the rolC-promoter derived from the nucleotide sequence 11286 up to 12132 between the open reading frames 11 and 12 of the TL-DNA from an *Agrobacterium rhizogenes* plasmid pRiA4 (Slightom et al. 1986, J. Biol. Chem. 261, 108–121) is isolated from plasmid pRiA4 using standard PCR technology in such a manner that the truncated rolC promoter sequence is amplified with a BamHI site created on both sides of the sequence. This amplified fragment is then fused to the GUS gene of plasmid pMOG452 resulting in binary plasmid pMOG679 (FIG. 8). The orientation of the truncated rolC promoter in relation to the GUS gene is checked with restriction analysis.
g) Construction of pMOG583; a binary vector containing the 35S promoter and a Barstar gene The barstar gene from *Bacillus amyloliguefaciens* is derived from plasmid pMT316 (Hartley, 1988, J. Mol. Biol. 202, 913–915). The plasmid pMT316 is linearized with HindIII followed by ligation in the presence of a synthetic adaptor, thus replacing the HindIII restriction site with a BamHI restriction site. The barstar gene is then isolated as a BamHI fragment and cloned into the BamHI site of pMOG180. The entire expression construct is then cloned as a EcoRI/HindIII fragment into the multiple cloning site of the binary vector pMOG22, resulting in plasmid pMOG583 (FIG. 9).

h) Construction of pMOG716; a binary vector containing the rolD Promoter and a Barstar gene The barstar gene from *Bacillus amyloliguefaciens* is derived from plasmid pMT316 (Hartley, 1988, J. Mol. Biol. 202, 913–915). The plasmid pMT316 is linearized with HindIII followed by ligation in the presence of a synthetic adaptor, thus replacing the HindIII restriction site with a BamHI restriction site. The barstar gene is then isolated as a BamHI fragment and cloned before the nopaline synthase terminator into the BamHI site of pMOG707. The 373 bp 5' flanking region of rolD of plasmid pRiA4 (ORF15 in Slightom et al. 1986, J. Biol. Chem. 261, 108–121) is then cloned in front of the barstar gene after which the entire cassette is transferred to pMOG22, resulting in binary vector pMOG716 (FIG. 10).

i) Construction of pMOG718; a binary vector containing two barstar genes regulated by a 35S and a rolD promoter respectively.

Figure 11:
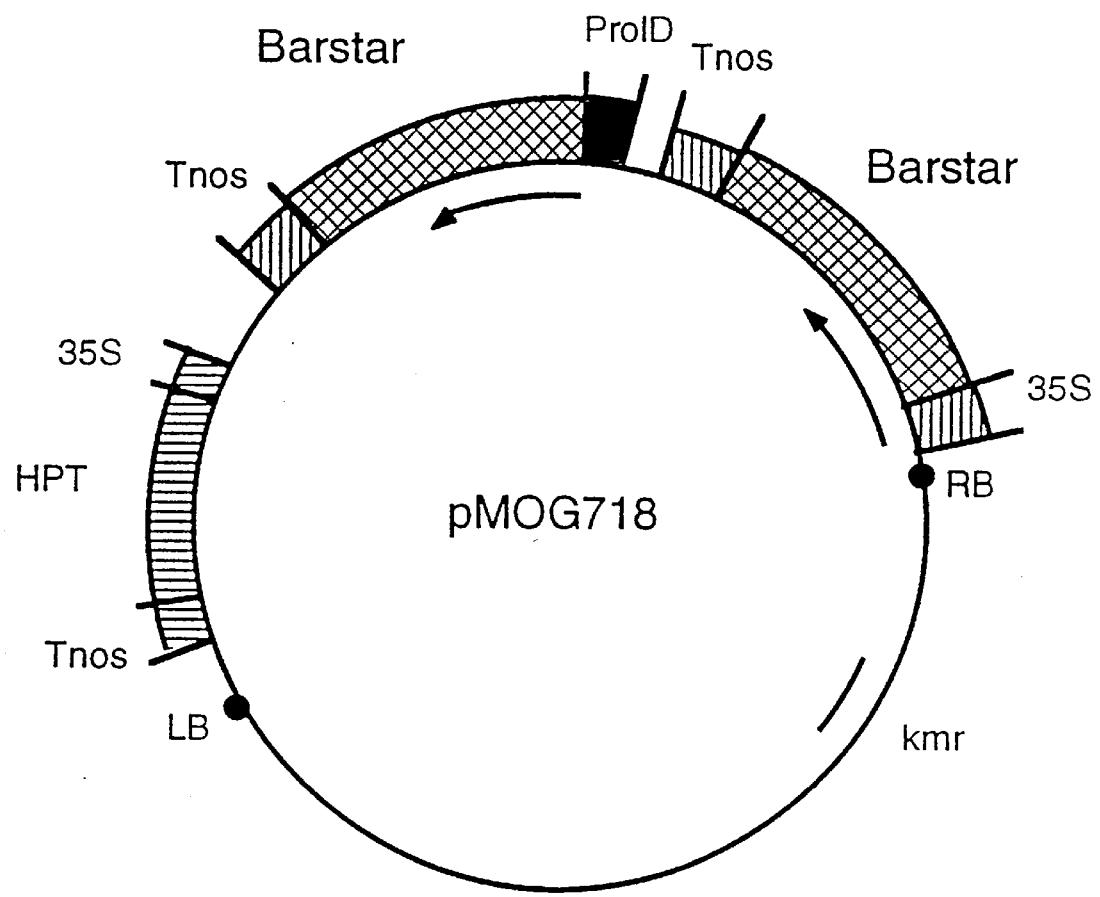
FIG. 11. Binary vector pMOG718. This plasmid is a derivative of pMOG22 and contains two barstar genes, one regulated by a 35S promoter and one regulated by a rolD promoter.

The 35S-Barstar and rolD-Barstar fragments, as described in Examples III g & h respectively, can also be used to construct a binary vector containing two barstar genes, each regulated by a different promoter of type B, both fused to a terminator functional in plant cells. For this purpose, the promoter-Barstar-terminator fragments can be used by someone skilled in the art for tandem cloning in pMOG23, resulting in binary vector pMOG718 (FIG. 11).

j) Construction of pMOG589; a binary vector containing a promoterless Barnase gene.

From pMOG23, the EcoRI-BalII fragment is isolated, containing the multiple cloning site and the right border sequences, and cloned into pMTL26/2 (Example Ic) resulting in pMOG584. Subsequently, the nos terminator is isolated from pMOG18 as a BamHI-HindIII fragment, ligated to a synthetic adaptor such that the HindIII site is not recovered and an EcoRI site is introduced and subsequently cloned into pMOG584 as a BamHI-EcoRI fragment, resulting in pMOG585.

Figure 12:
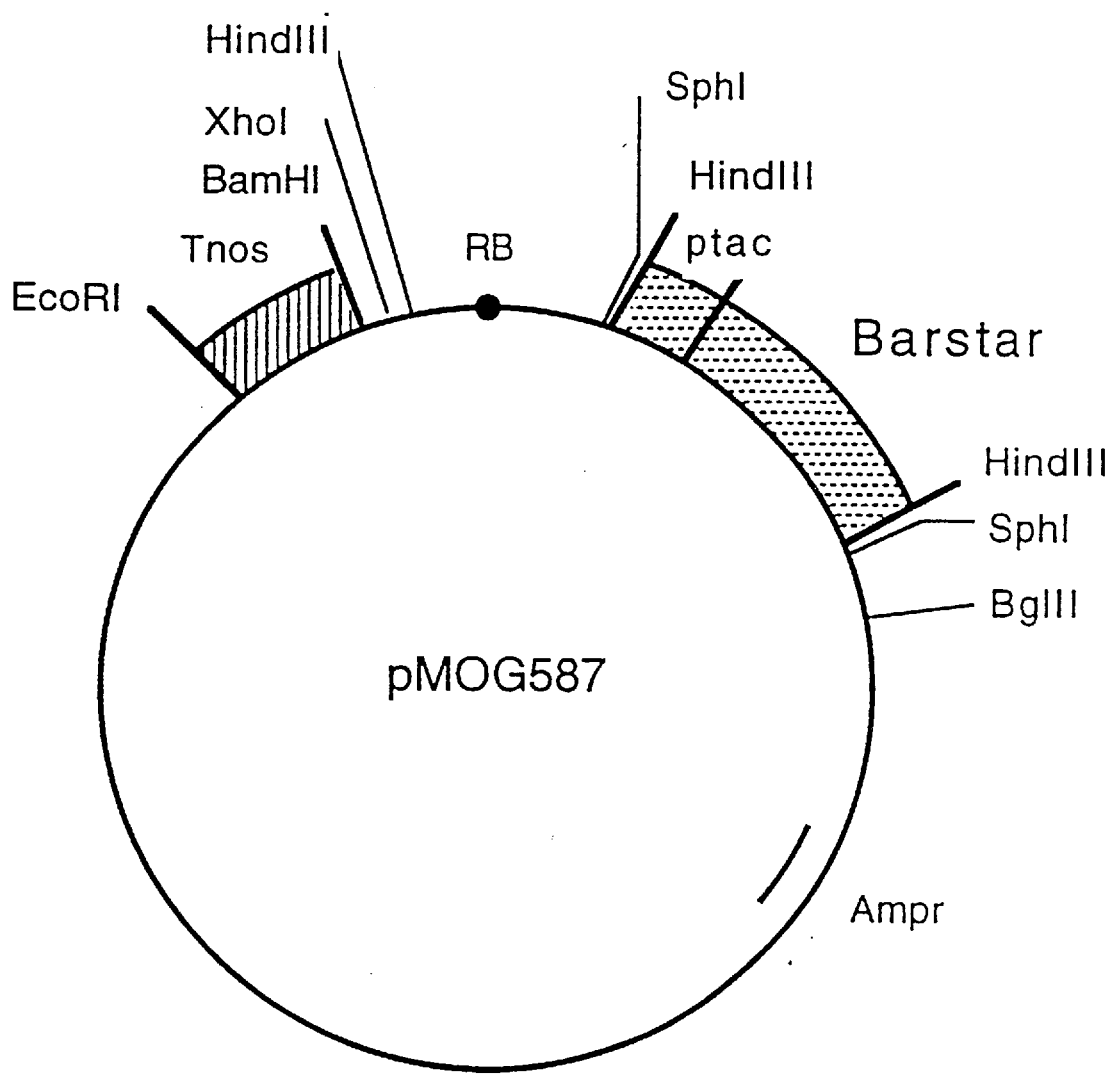
FIG. 12. Plasmid pMOG587. Intermediate vector prepared for insertion of barnase gene and containing the barstar gene with a bacterial promoter and a nos-terminator.

To overcome potential leaky activity of the barnase gene in bacteria, a gene encoding barstar under the control of a bacterial promoter is cloned into vectors, outside the T-DNA in case of binary vectors. For this purpose, the plasmid pMT316 (Hartley, 1988, J. Mol. Biol. 202, 913–915) is linearised with EcoRI and a synthetic adaptor is ligated, such that the EcoRI site is not recovered and a HindIII site is introduced. This modified fragment is then cloned as HindIII fragment into vector pMTL24 (Chambers et al. 1988, Gene 68, 139–149), thus creating pMOG586. The XhoI and BamHI sites present in the tac promoter region are removed by blunt-ending these sites with Klenow polymerase. The tac/Barstar sequence is isolated as a SphI fragment and inserted into plasmid pMOG585 in the SphI site between the right border and the BglII site, resulting in plasmid pMOG587 (FIG. 12).

Figure 13:
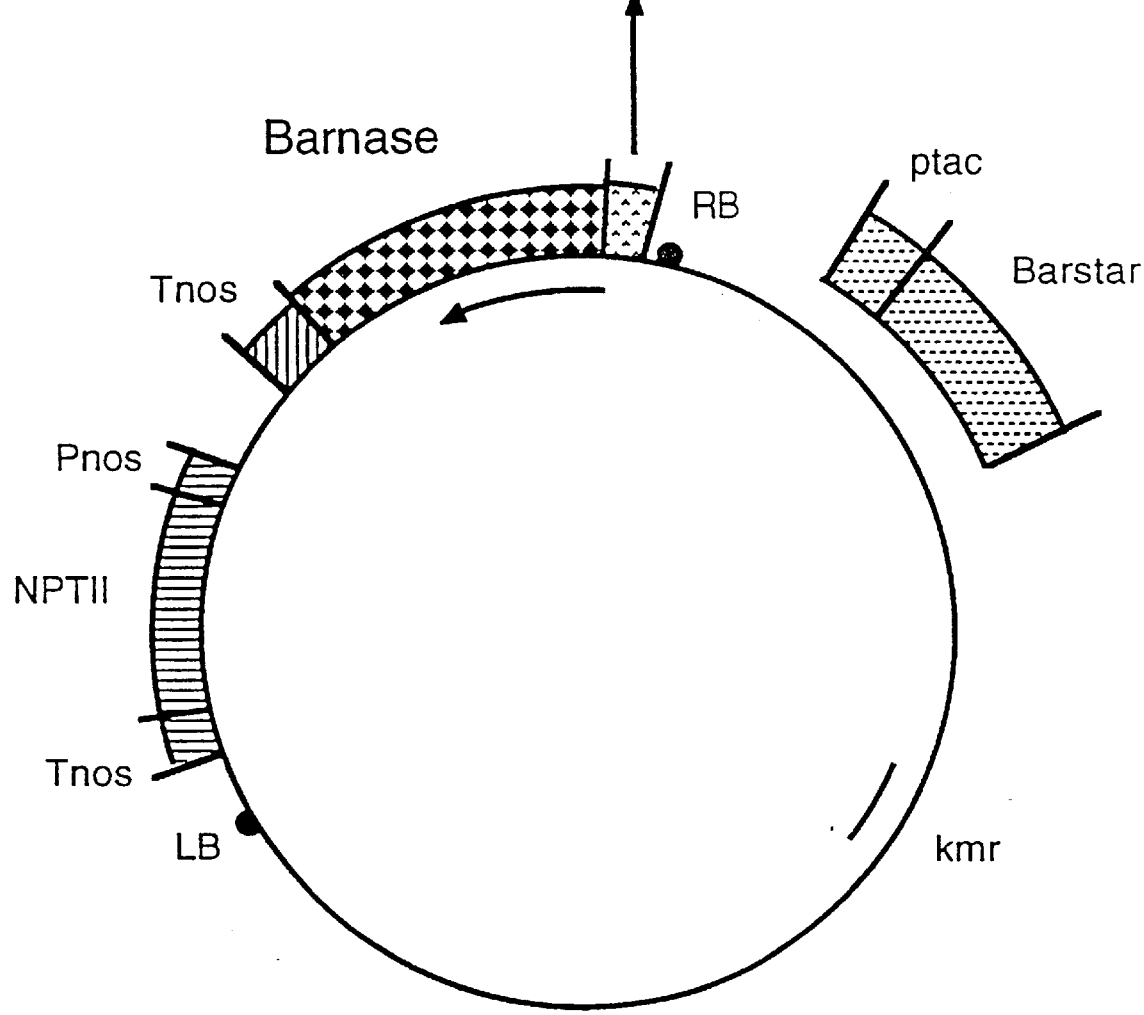
FIG. 13. Binary vectors pMOG589, pMOG591, pMOG717 & pMOG699. These plasmids are derivatives of pMOG23 and contain either a promoterless barnase gene directly after the right border (pMOG589), a multiple cloning site for insertion of a range of different promoter-A type regulatory sequences (pMOG591), a truncated rolC promoter and a barnase gene (pMOG717) or a truncated Δ0.3 TobRB7 promoter and a barnase gene (pMOG699). To prevent possible harmfull effects of the barnase gene during cloning procedures in bacteria, either a barstar gene with a bacterial promoter can be inserted outside the T-DNA borders, or alternatively, an intron can be inserted in the coding region of the barnase gene. In the latter case the pMOG numbers have an i added (e.g. pMOG699i).

The barnase gene from *Bacillus amyloliguefaciens* is derived from plasmid pMT416 (Hartley, 1988, J. Mol. Biol. 202, 913–915). The gene coding for mature barnase is amplified using PCR technology with a primer set that introduces a XhoI restriction site and ATG at the 5' site of barnase and a BamHI site at the 3' site. This fragment is sequenced to check for the correct coding sequence of barnase and ligated into pMOG587 that was linearized with BamHI and XhoI resulting in pMOG588. Both pMOG23 and pMOG588 are digested with EcoRI and BglII and the resulting fragments are ligated and linearized again with BglII. Fragments of the correct size are ligated into BglII-digested pMOG23 to form the binary vector pMOG589 (FIG. 13).

Alternatively, to overcome potential leaky activity of the barnase gene in bacteria, an intron can be introduced into the barnase coding sequence as described below; the Barnase gene is now isolated from plasmid pMT416 by PCR, using the following primer combination; 5' primer: 5' CTGCTC-GAGCCTAGGCACAGGTTATCAACACGTTTG 3' (SEQIDNO:3)

3' primer: 5' CGGACTCTGGATCCGGAAAGTG 3' (SEQIDNO:4) hereby introducing both a XhoI and an AvrII site at the 5' end of the gene and a BamHI site at the 3' end. This fragment is subcloned as XhoI/BamHI fragment into pMOG707. The 2nd intron of ST-LS1 from Solanum tuberosum was isolated by a PCR on plasmid p35S GUS INT (Vancanneyt et al. 1990, Mol Gen Genet 220:245–250) thereby introducing AvrII sites at both ends of the intron. This intron was inserted as AvrII fragment in the Barnase gene. The Barnase gene including the intron was re-isolated from this plasmid by PCR using the following primers;

5' primer: 5' CTTACTCGAGCCATGGTAAGTTTCTGC 3' (SEQIDNO:5)

3' primer: 5' CGGACTCTGGATCCGGAAAGTG 3' (SEQIDNO:6) thereby introducing a startcodon upstream of the ST-LS1 intron sequence. This fragment is then subcloned as XhoI/BamHI fragment into pMOG707 which is linearized with BamHI and partially cut with XhoI (thus the XbaI site is retained in the polylinker sequence) resulting in pMOG588i (FIG. 13). Both pMOG23 and pMOG588i are digested with EcoRI and BalI and the resulting fragments are ligated and linearized again with BalII. Fragments of the correct size are ligated into BalII-digested pMOG23 to form the binary vector pMOG589i (FIG. 13). The "pMOG————i" notation will be used throughout this patent application to indicate the presence of an intron in the barnase gene.

The choice between using a barnase containing an intron or a barstar gene outside the borders of the T-DNA for construction of the binary vectors in this example, is not critical for this invention.

k) Construction of pMOG591i; a binary vector containing a multiple cloning site in front of a promoterless Barnase gene.

This construct is used to insert a range of different regulatory sequences as identified in Example XII. For this purpose, the synthetic multiple cloning site of pMOG588i between the 5' barnase sequence and the right border of the T-DNA can be extended. The resulting plasmid pMOG590i is used for the construction of binary vector pMOG591i (FIG. 13). This vector is then used to introduce promoter-A regulatory sequences in a transcriptional fusion with the gene coding for barnase.

l) Construction of pMOG717i; a binary vector containing a truncated rolC promoter and a barnase gene.

The truncated rolC promoter sequence that was described in Example IIIf, can be isolated from plasmid pRiA4 (Slightom et al. 1986, J. Biol. Chem. 261, 108–121) and is amplified with a XbaI site created at the 5' end and a NcoI site at the 3' end. This fragment can be cloned into pMOG588i leading to a transcriptional fusion between the truncated rolC promoter and the Barnase gene. This plasmid is used for the construction of binary vector pMOG717i (FIG. 13).

m) Construction of pMOG699; a binary vector containing a truncated promoter (Delta0.3TobRB7-5A) and a barnase aene The Delta0.3TobRB7-5A promoter sequence (Yamamoto et al. 1991, Plant Cell 3: 371–382) was isolated by a two-step PCR on genomic DNA isolated from tobacco. In the first PCR reaction, part of the TobRB7-5A gene is being isolated using the following primers:

5' primer: 5' CTCCAAATACTAGCTCAAAACC 3' (SEQIDNO:7)

3' primer: 5' CCTCACCATGGTTAGTTCTC 3' (SEQIDNO:8).

The resulting PCR product is used to isolate the Delta0.3TobRB7-5A fragment using the following primers:

5' primer: 5' CTTGAATTCTAGATAAGCT-TATCTAAAC 3' (SEQIDNO:9)

3' primer: 5' CCTCACCATGGTTAGTTCTC 3' (SEQIDNO:10).

Figure 14:
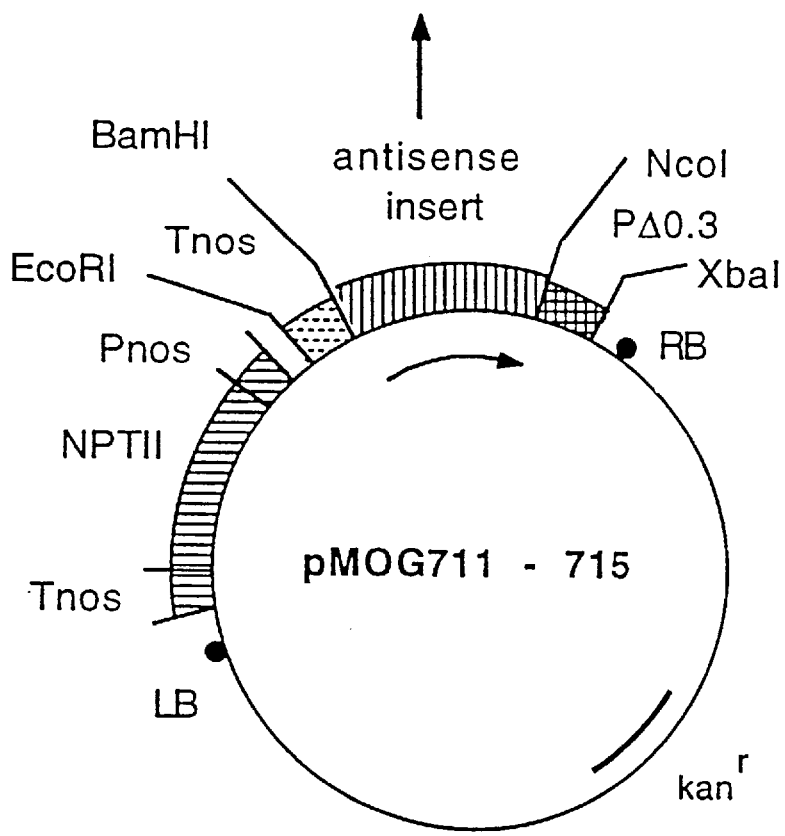
FIG. 14. Binary vectors pMOG711–pMOG715. These plasmids are derivatives of pMOG23 and contain a truncated Δ0.3 TobRB7 promoter and an antisense construct of a gene that is essential for cell viability.
Figure 15:
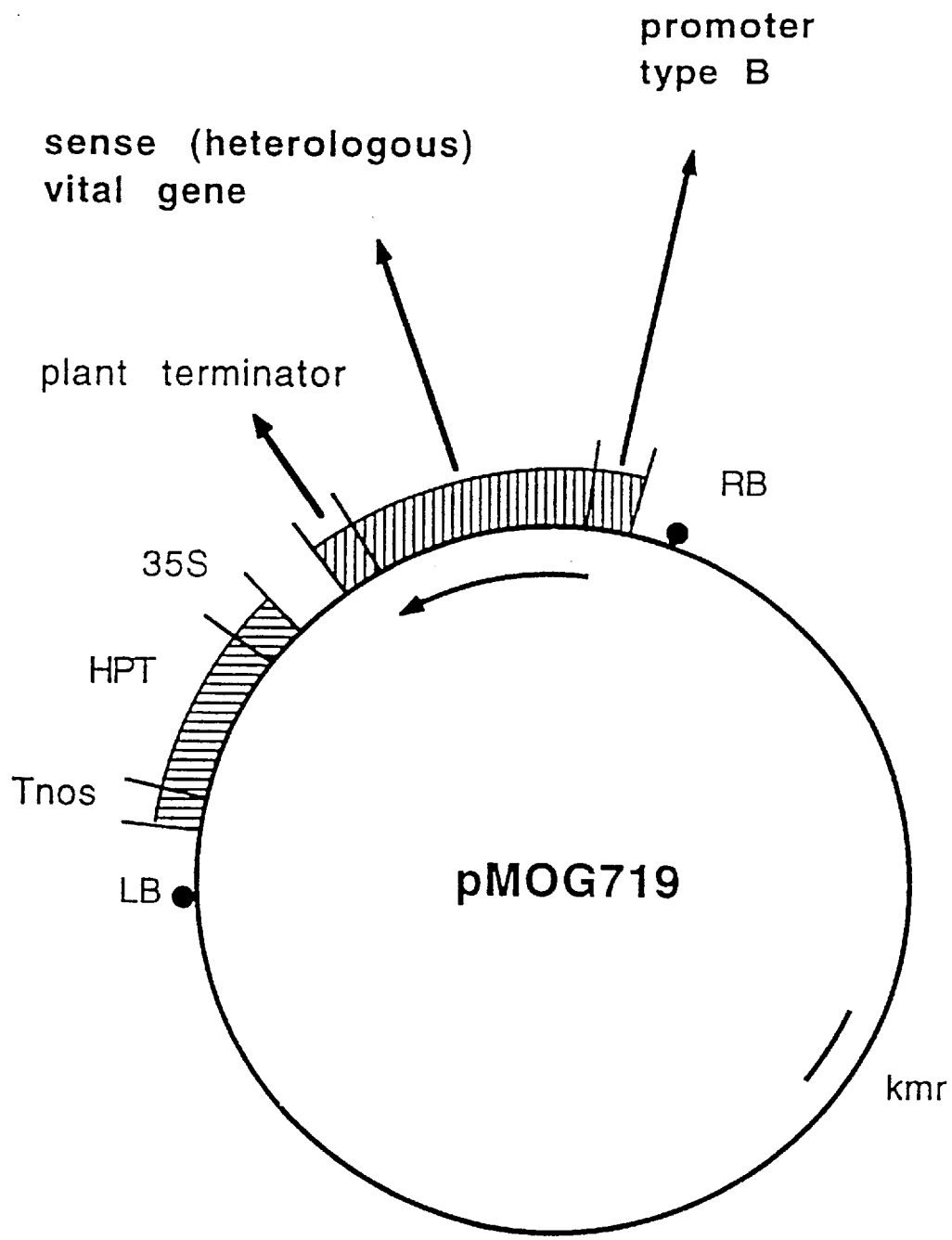
FIG. 15. Binary vector pMOG719. This drawing is a general illustration of a plasmid that can be used to introduce a heterologous vital gene, regulated by a promoter type B.
Figure 16:
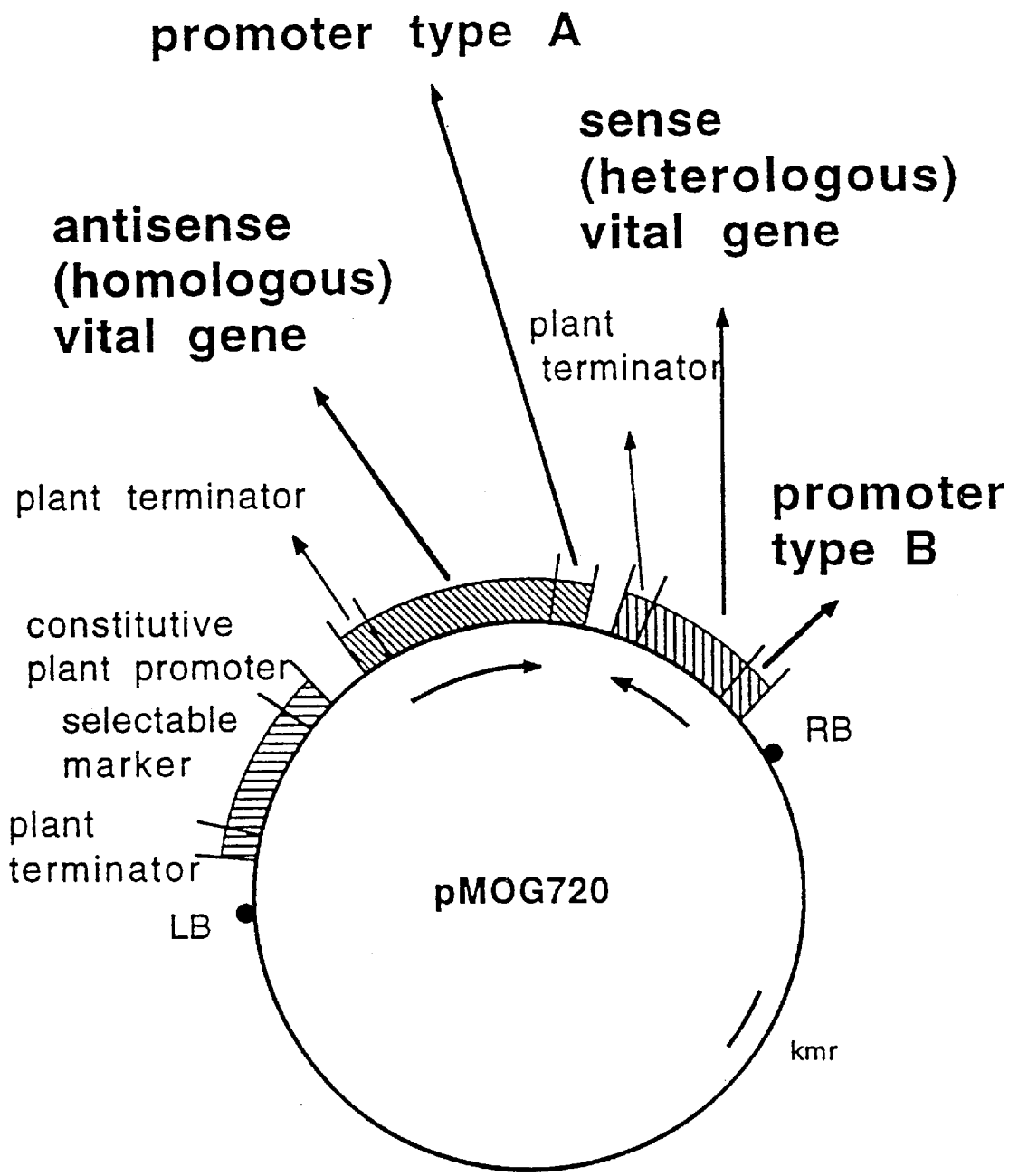
FIG. 16. Binary vector pMOG720. This drawing is a general illustration of a plasmid that contains complete antisense/sense two-component system for expression in plants to obtain nematode resistance.

The resulting PCR product is purified out of gel, blunt ended and subcloned into pUC9 (Vieira & Messing 1982 Gene 19; 259–268) which is then linearised with SmaI. Digestion of the resulting plasmid with XbaI and partially with NcoI yields the correct Delta0.3TobRB7-5A fragment which can be subcloned into pMOG588i. This plasmid is used for the construction of binary vector pMOG699i (FIG. 13).

n) Construction of DMOG711; a binary vector containing a truncated promoter (Delta0.3TobRB7-5A) and an antisense NADPH-CytP450 reductase ATR1 gene The clone for NADPH-cytochrome P450 reductase ATR1 (EMBL accession number X66016) is isolated from *Arabidopsis thaliana* var. Landsberg erecta using PCR technology on cDNA made of mRNA from this species. The primer set 5' GGCGGATCGGAGCGGGGAGCTGAAG 3' (SEQIDNO:11) and 5' GATACCATGGATCACCAGA-CATCTCTG 3' (SEQIDNO:12) is used to amplify the sequence of interest. This introduces a NcoI site on the N-terminus of the PCR fragment. Subsequently, the PCR fragment is digested with BamHI-NcoI and cloned antisense before the nopaline synthase terminator into pMOG707. The truncated promoter sequence Delta0.3TobRB7-5A (Yamamoto et al. 1991, Plant Cell 3; 371–382), isolated as described in Example IIIm, can then be inserted as a XbaI-NcoI fragment. The entire sequence is then cloned into the binary vector pMOG23 after digestion with EcoRI and one of the remaining unique restriction enzymes, resulting in binary vector pMOG711 (FIG. 14).

o) Construction of pMOG712; a binary vector containing a truncated promoter (Delta0.3TobRB7-5A) and an antisense NADPH-CytP450 reductase ATR2 gene The clone for NADPH-cytochrome P450 reductase ATR2 (EMBL accession number X66017) is isolated from *Arabidopsis thaliana* var. Landsberg erecta using PCR technology on cDNA made of mRNA from this species. The primer set 5' GGTTCTGGGGATCCAAAACGTGTCGAG 3' (SEQIDNO:13) and 5' GGCTTCCATGGTTTCGTTAC-CATACATC 3' (SEQIDNO:14) is used for amplification. This introduces both a BamHI and a NcoI flanking the PCR fragment. Subsequently, the PCR fragment is digested with BamHI-NcoI and cloned antisense before the nopaline synthase terminator into pMOG707. The truncated promoter sequence Delta0.3TobRB7-5A (Yamamoto et al. 1991, Plant Cell 3; 371–382), isolated as described in Example IIIm, can then be inserted as a XbaI-NcoI fragment. The entire sequence is then cloned into the binary vector pMOG23 after digestion with XhoI and partial digestion with EcoRI or, alternatively, after digestion with XbaI and partial digestion with EcoRI, resulting in binary vector pMOG712 (FIG. 14).

p) Construction of PMOG713; a binary vector containing a truncated promoter (Delta0.3TobRB7-5A) and an antisense glycerol-3-phosphate acyltransferase gene The clone for glycerol-3-phosphate acyltransferase ATS1 (EMBL accession number D00673) is isolated from *Arabidopsis thaliana* using PCR technology on cDNA made of mRNA from this species. The primer set 5' GCCCGG-GATCCGGTTTATCCACTCG 3' (SEQIDNO:15) and 5' GAGTATTTTCCATGGATTGTGTTTGTG 3' (SEQIDNO:16) is used for amplification. This introduces both a SmaI, BamHI and a NcoI flanking the ATS1 clone. Subsequently, the PCR fragment is digested with SmaI-NcoI and as such subcloned into pMOG445. (pMOG445 is a pUC18 derivative that contains, by insertion of an oligo adaptor in the multiple cloning site, the extra restriction sites ClaI, NcoI and BglII between EcoRI and SstI). Subsequently, the ATS1 clone is isolated after NcoI and partial BamHI digestion and subcloned antisense before the nopaline synthase terminator into pMOG707. The truncated promoter sequence Delta0.3TobRB7-5A (Yamamoto et al. 1991, Plant Cell 3; 371–382), isolated as described in Example IIIm, is then inserted as a XbaI-NcoI fragment. The entire sequence is then cloned into the binary vector pMOG23 after digestion with EcoRI and one of the remaining unique restriction enzymes, resulting in binary vector pMOG713 (FIG. 14).

q) Construction of pMOG714; a binary vector containing a truncated promoter (Delta0.3TobRB7-5A) and an antisense adenine nucleotide translocator gene The clone for the mitochondrial adenine nucleotide translocator (PANT1, EMBL accession number X57557; Winning et al. 1992 Plant J. 2; 763–773) is isolated from *Solanum tuberosum* using PCR technology on cDNA made of mRNA from this species. The primer set 5' GCTAGC-CGGATCCATCTGAGCTCCAG 3' (SEQIDNO:17) and 5' GACGTCCATGGCTGAATTAGCCACCACCG 3' (SEQIDNO:18) is used for amplification. This introduces both a BamHI and a NcoI flanking the PANT1 clone. Subsequently, the PCR fragment is digested with BamHI-NcoI and cloned antisense before the nopaline synthase terminator into pMOG707. The truncated promoter sequence Delta0.3TobRB7-5A (Yamamoto et al. 1991, Plant Cell 3; 371–382), isolated as described in Example IIIm, is then be inserted as a XbaI-NcoI fragment. The entire sequence is then cloned into the binary vector pMOG23 after digestion with EcoRI and one of the remaining unique restriction sites, resulting in binary vector pMOG714 (FIG. 14).

r) Construction of pMOG715; a binary vector containing a truncated promoter (Delta0.3TobRB7-5A) and an antisense ATP synthase gene The clone for the beta subunit of ATP synthase (Boutry & Chua 1985 EMBO J. 4; 2159–2165) is isolated from tobacco (*Nicotiana plumbaginifolia*) using PCR technology on cDNA made of mRNA from this species. The primer set 5' CCCTCCAGGATCCCTTCTCGGAGGCTTC 3' (SEQIDNO:19) and 5' GAAAAGAAAGCCATGGAACTT-TATAATC 3' (SEQIDNO:20) is used for amplification. This introduces both a BamHI and a NcoI flanking the ATP synthase clone. Subsequently, the PCR fragment is digested with BamHI-NcoI and cloned antisense before the nopaline synthase terminator into pMOG707. The truncated promoter sequence Delta0.3TobRB7-5A (Yamamoto et al. 1991, Plant Cell 3; 371–382), isolated as described in Example IIIm, is inserted as a XbaI-NcoI fragment. The entire sequence is then cloned into the binary vector pMOG23 after digestion with EcoRI and one of the remaining unique restriction sites, resulting in binary vector pMOG715 (FIG. 14).

s) Description of pMOG719, a binary plasmid containing promoter type B and sense heterologous vital gene combinations This description is given by way of general illustration; pMOG719 is a derivative of pMOG22 and is used for a first round of plant transformation, followed by transformation with a binary vector as described in Example III*n–r*. pMOG719 constructs contain a promoter-B fused to a sense gene that is coding for a protein or polypeptide that is functionally similar to the antisense gene from Example III*n–r* but is heterologous in nucleotide sequence (FIG. 15). Preferably, the nucleotide sequence identity of the transcripts encoded by the antisense transgene and the sense transgene is less than 90%, preferably less than 80%, yet more preferably less than 75%. The sense transgene is obtainable from a different species than the target species. As examples of such heterologous genes the following constructs are made:

the expression cassette of pMOG180 (Example I, 35S promoter/nos terminator) is transferred to pMOG22 as an EcoRI-HindIII fragment, resulting in pMOG22bis.

pMOG719-1: the gene coding for glycerol-3P-acyltransferase (Ishizaki et al. 1988 FEBS Lett. 238; 424–430, EMBL accession number Y00771) is isolated from squash cDNA using PCR amplification with the following primers 5' GCTTCCAGATCTATGGCG-GAG 3' (SEQIDNO:21) AND 5' GATTACCAAAA-GATCTGATGTTG 3' (SEQIDNO:22). The amplified fragment is digested with BamHI and cloned into the binary vector pMOG22bis which is linearized with BamHI, resulting in binary vector pMOG719-1. This vector is checked for the correct sense orientation of the G3PAT insert with restriction analyses, pMOG719-2: the gene coding for the adenine nucleotide translocator (Baker & Leaver 1985 Nucl. Acids Res. 13; 5857–5867, EMBL accession number X02842) is isolated from maize cDNA using PCR amplification with the following primers 5' GAATTCGGATCCT-GATGCCAGACCCCGCTCTGTG 3' (SEQIDNO:23) and 5' GGACCGGGATCCCACACTGCTCTTG 3' (SEQIDNO:24). The amplified fragment is digested with BamHI and cloned into the binary vector pMOG22bis, which was linearized with BamHI, resulting in binary vector pMOG719-2. This vector is checked for the correct sense orientation of the ANT insert with restriction analyses.

pMOG719-3: the gene coding for the beta subunit of ATP synthase (Winning et al. 1990 Nucl. Acids Res. 18; 5885, EMBL accession number X54233) is isolated from maize cDNA using PCR amplification with the following primers 5' CCCTGGATCCGGACCGGC-CATGGC 3' (SEQIDNO:25) and 5' CAAGCAAG-GATCCTCCTTATGAAGC 3' (SEQIDNO:26). The amplified fragment is blunt ended and subcloned into pUC9 (Vieira & Messing 1982 Gene 19; 259–268) which was linearized with SmaI and HinCII. The resulting vector is partially digested with BamHI and cloned into the binary vector pMOG22bis, resulting in binary vector pMOG719-3. This vector is checked for the correct sense orientation of the ATP synthase insert with restriction analyses.

EXAMPLE IV

Mobilisation of binary vectors into Agrobacterium

The binary vectors described in Example III are mobilized in a triparental mating with *E. coli* K-12 strain HB101 (containing plasmid RK2013) (Ditta et al., 1980, Proc. Nat. Acad. Sci. USA 77, 7347–7351), into *Agrobacterium tumefaciens* strains MOG101 (Example II) or LBA4404 (Hoekema et al. 1983, Nature 303, 179–180) that contains a plasmid with the virulence genes necessary for T-DNA transfer to plants.

EXAMPLE V

Plant Transformation a) Transformation of *Arabidopsis thaliana*

Arabidopsis is transformed by cocultivation of plant tissue with *Agrobacterium tumefaciens* strain MOG101 containing one of the binary vectors described in Example III. Transformation is carried out using cocultivation of *Arabidopsis thaliana* (ecotype C24) root segments as described by Valvekens et al. (1988, Proc. Nat. Acad. Sci. USA 85, 5536–5540). Transgenic plants are regenerated from shoots that grow on selection medium (containing either kanamycin or hygromycin, depending on the originating binary plasmid pMOG23 or pMOG22 respectively), rooted and transferred to germination medium or soil. Young plants are grown to maturity and allowed to self-pollinate and set seed.

b) Transformation of potato (*Solanum tuberosum* ssp.)

Potato is transformed by cocultivation of plant tissue with *Agrobacterium tumefaciens* strain LBA4404 containing one of the binary vectors described in Example III. Transformation is carried out using cocultivation of potato (*Solanum tuberosum* var. Desiree) tuber disks as described by Hoekema et al. 1989, Bio/Techn. 7, 273–278). Transgenic plants are regenerated from shoots that grow on selection medium (containing either kanamycin or hygromycin, depending on the originating binary plasmid pMOG22 or pMOG23), rooted, multiplied axenically by meristem cuttings and transferred to soil. Young plants are grown to maturity and allowed to develop tubers.

c) Transformation of tobacco (*Nicotiana tabacum* SR1)

Tobacco is transformed by cocultivation of plant tissue with *Agrobacterium tumefaciens* strain LBA4404 (Hoekema et al. 1983, Nature 303, 179–180) containing one of the binary vectors described in Example III. Transformation is carried out using cocultivation of tobacco (*Nicotiana tabacum* SR1) leaf disks as described by Horsch et al. 1985, Science 227, 1229–1231). Transgenic plants are regenerated from shoots that grow on selection medium (containing either kanamycin or hygromycin, depending on the originating binary plasmid pMOG22 or pMOG23), rooted and transferred to soil. Young plants are grown to maturity and allowed to self-pollinate and set seed.

EXAMPLE VI

Analysis of transgenic Arabidopsis plants for susceptibility to PPN

Transgenic Arabidopsis plants are assayed both in vitro or in soil for resistance against *M. incognita* or the cyst nematode *H. schachtii*. For in vitro analysis, seeds are surface sterilized, grown and inoculated as described by Sijmons et al. (1991, Plant J. 1, 245–254). Two weeks after infection, the root systems can be scored visually for the number of successful infections and compared to wild type Arabidopysis plants. Plant lines are considered resistant when they show a significantly decreased susceptibility to PPN (i.e. a significant decrease in the number of females found on control roots). For soil-grown plants, seedlings are germinated on selective medium (10 mg/l hygromycin or 50 mg/l kanmaycin). Resistant seedlings are transferred to soil/sand mixtures (1:3 v/v) in 1×1×6 cm transparent plastic tubes. Once the rozettes are well developed (ca. 14 days) the containers are inoculated with ca. 300 hatched J2 of *H. schachtii* each. Hatching of *H. schachtii* is stimulated by submerging cysts for several days in a 3 mM $ZnCl_2$ solution at a temperature of ca. 20° C. Eighteen days after inoculation, the roots are carefully removed from the soil/sand mixture and stained with acid fuchsin (Dropkin, 1989 in: Introduction to plant nematology, 2nd edition, Wiley & Sons, New York). In this assay, susceptible plants score a mean of 17 cysts per root system (range 4–40 cyst per root system). A genotype is considered resistant when the mean number of cysts is reduced to 2 per root system. Similarly, plants can be inoculated with hatched J2 of *M. incognita* or with egg-masses that are mixed through the soil/sand mixture. The plants are then be scored for the presence of galls which are clearly visible after the soil/sand mixture is removed from the roots.

EXAMPLE VII

Analysis of Transgenic Tobacco Plants for Susceptibility to PPN

For analysis of nematode resistance, the soil is preinfected with *M. incognita* egg masses. This inoculum can be produced by maintaining a stock culture of *M. incognita* on soil grown celery plants (*Apium graveolens*) under standard greenhouse conditions, below 25° C. Mature celery root systems, containing a high number of root knots and mature females of *M. incognita*, are carefully dusted off to remove the soil, homogenized briefly in a Waring blendor (2 seconds) and weighed in portions of 60 gram. These root samples are mixed with 1 kg sand:potting soil (1:1) mixtures and used for growth of transgenic tobacco plants for 6 weeks. For each genotype, at least 100 indivdual plants are used for each test. The soil/sand mixture is then carefully washed away and the number of galls/root system is counted with a binocular. In this assay, control plants have a mean of 25±15 galls. A genotype is considered resistant when the mean number of galls is reduced to 2 per root system.

EXAMPLE VIII

Analysis of transgenic potato plants for susceptibility to PPN

Transgenic potato plants are assayed for resistance against *M. incognita* using soil that is preinfected with *Mi. incognita* egg masses mixed with sand (1:3 w/w), growing the potato plants in that soil mixture for 6 weeks and, after removing the soil, counting the developed number of galls on a root system. Alternatively, to assay for resistance against Globodera ssp. a closed container is used. For this assay, three replicate 2–4 cm tubers are transferred to soil which is pre-inoculated with cysts from *G. rostochiensis* or *G. pallida* in transparent containers. The peripheral root systems are analyzed visually 7–8 weeks after germination for the presence of cysts. A genotype will be scored as resistant if none of the three replicates had cysts and susceptible if at least one of the three replicates shows cysts.

EXAMPLE IX

Analysis of GUS activity inside feeding structures of plants transgenic for the chimaeric 35S/GUS construct.

Plant lines transgenic for the T-DNA of constructs pMOG25 or pMOG28 (35S/GUS) are used for infection with cyst-or root-knot nematodes and subsequent analysis of GUS activity (Jefferson, 1987, Plant Mol. Biol. Reporter 5, 387–405) inside the feeding structures. Arabidopsis is especially suitable for this purpose as these plants are readily used in monoxenic cultures with both *Heterodera schachtii* and *Meloidogyne* incognita (Sijmons et al. 1991 Plant J. 1, 245–254). The development of the feeding structure is exceptionally well visible in this plant species when grown in agar plates. Agar pieces containing infected root parts are cut directly from petridishes without any disturbance of the nematode-plant interaction and used directly for histochemical GUS staining at 37° C. with the substrate 5-bromo-4-chloro-3-indolyl-glucuronide (X-Glu) in a buffer containing the following components: 100 mM NaPi pH 7.0 10 mM $Na_2EDTA$, 0.1% Triton X100, 2.1 µg/ml ferricyanide, 1.6 µg/ml ferrocyanide. With this model plant system, the down regulation of the 35S promoter activity is demonstrated clearly at the cellular level. There is no detectable GUS activity (hence no 35S-promoter activity) in any of the cells comprising the feeding structure, even after prolonged staining with X-Glu. On the contrary in uninfected roots GUS activity is found in all root parts and is especially high in young root tissue and the vascular cylinder. At late stages of infection of Arabidogsis with *M. incognita*, the down-regulation of the 35S promoter extends even beyond the feeding structure.

Transgenic tobacco plants are soil inoculated with *Globodera tabacum* or *M. incognita* and analyzed after proper development of feeding structures. For this purpose, roots are carefully washed for removal of soil, incubated with X-Glu assay buffer and double stained for detection of the nematodes with acid fuchsin staining (Dropkin, 1989).

Similar experiments are carried out with transgenic potato after soil inoculation with *Globodera rostochiensis, G. pallida* or *M. incognita*. In all cases, GUS activity is not detected inside feeding structures while uninfected root parts showed expression expected for the 35S promoter. Thus, the CaMV35S promoter fits the requirements explained in this application for a promoter of type B.

EXAMPLE X

Analysis of GUS activity inside feeding structures of plants transgenic for the chimaeric rolD/GUS construct.

Plant lines transgenic for the T-DNA of construct pMOG630 (rolD/GUS) are used for infection with cyst- or root-knot nematodes and subsequent analysis of GUS activity as described in the previous Example. Again here, the down regulation of the rolD promoter activity is demonstrated clearly at the cellular level. There is no detectable GUS activity (hence no rolD-promoter activity) in any of the cells comprising the feeding structure, even after prolonged staining with X-Glu. On the contrary in uninfected roots, GUS activity is found in all root parts and is especially high in young root tissue including the vascular cylinder, epidermis and root hairs. Thus, the *Agrobacterium rhizogenes* rolD-promoter fits the requirements explained in this application for a promoter of type B.

EXAMPLE XI

Analysis of GUS activity inside feeding structures of plants transgenic for the chimaeric truncated-rolC/GUS construct.

Plant lines transgenic for the T-DNA of construct pMOG679 (truncated rolC/GUS) are used for infection with cyst- or root-knot nematodes and subsequent analysis of GUS activity as described in the Example VI. In contrast with the 35S or the rolD promoter but also in contrast with several other promoters that were tested under similar conditions, a 5' truncated rolc-promoter/GUS fusion gives rise to a blue precipitate inside the feeding structure when the appropriate substrates are added. Thus, the *Aprobacterium rhizogenes* 5' truncated rolC-promoter fits the requirements explained in this application for a promoter of type A.

EXAMPLE XII

Identification of promoter-A type regulatory sequences in NFS of transgenic plants a) Transformation of Arabidopsis with pMOG452 Arabidopsis is transformed with Agrobacterium strain MOG101 containing the binary vector pMOG452 (promoterless GUS fused to the right border of the T-DNA) using the procedure as described in Example V.

b) Analysis of GUS activity inside feeding structures of plants transgenic for the promoterless GUS construct Transgenic plant lines (pMOG452, T2 or later generations) are used for infection with PPN and subsequent GUS analysis as described in Example IX. The results from such a screening experiment after inoculation with *H. schachtii* showed a surprisingly high number of plants with GUS activity inside the syncytia and low or no GUS actitivy in other plant parts, thus indicating that regulatory sequences that drive gene activity in the NFS are tagged with the GUS gene and therefor amenable to rapid isolation of such regulatory sequences. One in 13 independent transgenic plant lines indicated a tagged promoter that was active only in roots and that remained active inside the NFS. This could be confirmed with Arabidopsis plants transgenic for a promoterless GUS construct as described by (Topping et al., 1991, Developm. 112, 1009–1019). Two in 25 transgenic plant lines demonstrated GUS activity in cells comprising the NFS. This high frequency illustrates the feasability to tag, and therefore to isolate, regulatory sequences that fulfil the requirements of promoter-A. The reverse situation (GUS activity in healthy vascular cylinder but down-regulated inside developing feeding structures) was observed with even higher frequencies, and therefor the method is in principle also suitable for identification of regulatory sequences that fit the requirements of promoter-B types.

c) Isolation of promoter-A-type regulatory sequences from transgenic plants expressina GUS inside NFS Transgenic plant lines that express GUS activity inside NFS and preferably low or no activity in other tissues are selected and used for isolation of genomic DNA. Regulatory sequences upstream (5') of the integrated GUS gene are isolated with the following steps, using inverted PCR (Does et al. 1991, Plant Mol. Biol. 17, 151–153) with the primers 5' CCA GAC TGA ATG CCC ACA GGC 3' (SEQIDNO:27) and 5' GGT GAC GCA TGT CGC GCA AG 3' (SEQIDNO:28). The amplified fragment is used to screen a genomic library of Arabidopsis for the isolation of genomic clones containing regulatory sequences that fit the requirements of promoter-A. Alternatively, the first 200 bp of the GUS gene can be used to probe a genomic bank made from the selected plants.

EXAMPLE XIII

Synthesis of Barstar in transgenic plants, controled by regulatory sequences of type B promoters.

For western analysis of plants expressing the Barstar gene, an antiserum against Barstar is used that is produced in the following manner:

the most antigenic determinants of the Barstar protein is determined with three different prediction methods, based on hydrophilicity, flexibility and beta turns. Based on this analysis, three peptides are synthesized using an automated peptide synthesizer with the following amino acid sequence;

a) Ala-Glu-Ser-Val-Leu-Gln-Val-Phe-Arg-Glu-Ala-Lys-Ala-Glu- Gly (SEQIDNO:29)
b) Arg-Gln-Phe-Glu-Gln-Ser-Lys-Gln-Leu-Thr-Glu-Asn-Gly-Ala- Glu (SEQIDNO:30)
c) Leu-Lys-Lys-Glu-Leu-Ala-Leu-Pro-Glu-Tyr-Tyr-Gly-Asn-Leu- Asp (SEQIDNO:31).

These peptides are purified and 1.5 mg of each is coupled to 7.5 mg bovine serum albumin (BSA) using glutaraldehyde. The resulting conjugates were analyzed and contained 7.5 mole peptide (a) per mole BSA, 10.0 mole peptide (b) per mole BSA and 6.7 mole peptide (c) per mole BSA. The conjugates are dissolved in 50 mM Hepes, 100 mM NaCl with a final concentration of 1 mg/ml and mixed. Rabbits are injected with 0.15 ml mixed conjugates in Freunds complete adjuvans and boostered three times with 0.15 ml mixed conjugates in incomplete Freunds adjuvans. The resulting serum is partially purified for the antibody fraction and stored at −80° C. This serum is used in 5,000–10,000 dilutions in the presence of 5% defatted dry milk in phosphate buffered saline, 1% Tween 20, 0.5% Triton-X100. For western analysis, crude plant extracts are seperated on 10–27% gradient SDS-PAGE followed by electroblotting to nitrocellulose. The Barstar antibodies are detected with goat-anti-rabbit-peroxidase conjugates and visualized with the Amersham (UK) ECL-detection system.

The choice of Arabidopsis, tobacco and potato for introduction of the barstar and barnase expression constructs was based on the excellent properties of Arabidopsis to analyze plant-nematode interactions (Sijmons et al. 1991, Plant J. 1, 245–254), or the excellent transformation protocols available for tobacco and potato and by no means limits the scope of plant species to which this invention applies.

Arabidopsis is transformed with Agrobacterium strain MOG101 containing the binary vector pMOG583 or alternatively pMOG716 or alternatively pMOG718, all described in Example III, using procedures as described in Example V*a*. Transformants are regenerated on selective media containing 10 mg/l hygromycin. All hygromycin resistant plants are allowed to self pollinate and the resulting seed batches are germinated on hygromycin and tested for expression of the barstar gene by means of western analysis using antibodies against BSA-Barstar conjugates. Representative plant lines for high, medium and low expression are used for the second round of transformation.

Tobacco and potato are transformed with Agrobacterium strain LBA4404 containing the binary vector pMOG583 or alternatively pMOG716 or alternatively pMOG718, all described in Example III, using procedures as described in Example V*b* and V*c*. Transformants are regenerated on selective media and resistant plants are allowed to self pollinate or clonally propagated. In case of tobacco, the resulting seed batches are germinated on selective media and tested for expression of the barstar gene by means of western analysis using antibodies against barstar. The clonally propagated potato clones are assayed for Barstar expression after transfer of the plants to soil. Representative plant lines for high, medium and low expression are used for the second round of transformation.

EXAMPLE XIV

Introduction of promoterless Barnase DNA sequences in plants expressing Barstar from Example XIII and analysis of reduced susceptibility to PPN a) Transformation of Arabidopsis with pMOG589i The selected Arabidopsis plant lines from Example XIII, which express the Barstar gene, are used for transformation with Agrobacterium strain MOG101 containing the binary vector pMOG589i (Example III) using the procedure as described in Example VI. The regeneration of transformants is now done on 50 mg/1 kanamycin-containing media. All kanamycin-resistant regenerants are grown to maturity, allowed to self pollinate and analyzed for deviant phenotypes. Seeds from all plants with normal phenotype are germinated on kanamycin and grown to produce a next generation of seeds. A next round of germination on kanamycin-containing medium allows identification of plant lines homozygous for the NPTII gene.

b) Analysis of transgenic Arabidopsis for susceptibility to PPN

Plants produced with procedures as described in Example XIVa are used to establish their degree of susceptibility to PPN as described in Example VI. From these analyses, several plant lines are identified that show a decreased susceptibility to PPN (i.e. a decrease in the number of cysts with a mean of less than 10 cysts per root system), and a few lines were found to be resistant (i.e. mean less than 2 cysts per root system) especially among those lines that were selected for their high expression of barstar in Example XIII. Also, a number of abbarent phenotypes (e.g. reduced viability, sterile, non flowering, small root systems) are observed, possibly as a result of local expression of the barnase gene. Regulatory sequences upstream (5') of the integrated Barnase gene are isolated using inverted PCR (Does et al. 1991, Plant Mol. Biol. 17, 151–153). The amplified fragment is used to screen a genomic library of Arabidopsis for the isolation of genomic clones containing regulatory sequences that fit the requirements of promoter-A. Alternatively, the barnase gene is used to probe a genomic bank made from the selected plants.

c) Transformation of tobacco and potato with pMOG591bis

Regulatory sequences that are identified through procedures described in this example can be used for insertion in the multiple cloning site of pMOG591i (Example III), thus creating binary vector pMOG591bis. This vector is then be used for a second round of plant transformation, e.g. tobacco or potato plants that are selected for high Barstar expression in Example XIII. The resulting double transformants can be assayed for reduced susceptibility to PPN as described in Example VII and VIII.

EXAMPLE XV

Introduction of truncated rolC promoter/Barnase DNA sequences in plants expressing Barstar The selected plant lines from Example XIII are used for transformation with Aarobacterium strain MOG101 or LBA4404 containing the binary vector pMOG717i (truncated rolC/Barnase; Example III) using the procedures of Example VI. The regeneration of transformants is now done on kanamycin-containing media. All kanamycin-resistant regenerants are grown to maturity, allowed to self pollinate or form tubers (depending on the species) and analyzed for deviant phenotypes. For self-pollinating species, all plants with a normal phenotype are germinated on kanamycin and grown to produce a next generation of seeds. A next round of germination on kanamycin-containing medium allows identification of plant lines homozygous for the NPTII gene. In case of potato, transgenic plant lines are clonally propagated.

b) Analysis of double transgenic plant lines for susceptibility to PPN

The plants that are now transgenic for the Barstar gene (either provided by pMOG 583 or pMOG716 or pMOG718) and the Barnase gene (pMOG717i) are assayed for their degree of susceptibility to PPN as described in Example VI–VIII. From these analyses, plant lines are identified that show a significantly decreased susceptibility to PPN (i.e. a significant decrease in the number of cysts or galls compared to control roots), especially among those lines that were selected for their high expression of barstar in Example XIII.

EXAMPLE XVI

Introduction of Delta0.3TobRB7-5A promoter/ Barnase DNA sequences in plants expressing Barstar The selected plant lines from Example XIII are used for transformation with Agrobacterium strain MOG101 or LBA4404 containing the binary vector pMOG699i (Example III) using procedures as described in Example V. The regeneration of transformants is now done on kanamycin-containing media. All kanamycin-resistant regenerants are grown to maturity, allowed to self pollinate or form tubers (depending on the species) and analyzed for deviant phenotypes. For self-pollinating species, all plants with a normal phenotype are germinated on kanamycin and grown to produce a next generation of seeds. A next round of germination on kanamycin-containing medium allows identification of plant lines homozygous for the NPTII gene. In case of potato, transgenic plant lines are clonally propagated.

b) Analysis of double transgenic plant lines for susceptibility to PPN

The plants that are now transgenic for both the Barstar (either PMOG 583 or pMOG716 or pMOG718) and the Barnase construct (pMOG699i) can be assayed for their degree of susceptibility to PPN as described in Example VI–VIII. From these analyses, plant lines are identified that show a significantly decreased susceptibility to *M.incognita* (i.e. a significant decrease in the number of galls compared to control roots), especially among those lines that were selected for their high expression of barstar in Example XIII.

EXAMPLE XVII

Engineering reduced susceptibility to PPN with a single round of transformation Alternatively, binary vectors can be constructed that contain both expression cassettes for regulated expression of Barstar and Barnase, from DNA fragments described in Examples III (g)–(m) in ways that are applicable to the general description of this patent as illustrated in FIG. 1. Such binary vectors can then be used to engineer plants with reduced susceptibility to PPN in a single round of transformation and analysis of plant lines as described in Example VI–VIII.

EXAMPLE XVIII

Engineering reduced susceptibility to PPN using promoter A/antisense homologous vital gene and promoter B/sense heterologous vital gene binary constructs.

These examples are based on the same concept for a two-component system as is generally illustrated in FIG. 1. It involves the local (feeding structure) antisense expression of a homologous gene (preferably isolated from the target species) that is vital for plant cell metabolism and expression of a second transgene which when expressed is capable of neutralizing or partially neutralizing the effect caused by the first transgene and is in effect a sense construct of a heterologous gene and is expressed in cells outside the feeding structure.

a) Introduction of chimearic DNA sequences of the Delta0.3 TobRB7 promoter and the antisense NADPH-Cytochrome P450 ATR1 gene for specific regression of the nematode-induced feeding structures in Arabidopsis.

Arabidopsis plants transgenic for a construct of type B-promoter and a heterologous gene for NADPH-CytP450 reductase, is used for a second round of transformation by cocultivation of plant tissue with *Agrobacterium tumefaciens* strain MOG101 containing the binary vector pMOG711 as described in Example V. Transgenic plants are regenerated from shoots that grow on selection medium, rooted and transferred to germination medium or soil. Young plants are grown to maturity and allowed to self-pollinate and set seed. Plants transgenic for both the sense and the antisense construct are analyzed for reduced susceptibility to PPN as described.

b) Introduction of chimearic DNA sequences of the Delta0.3 TobRB7 promoter and the antisense NADPH-Cytochrome P450 ATR2 gene for specific regression of the nematode-induced feeding structures in Arabidopsis.

Arabidopsis plants transgenic for a construct of type B-promoter and a heterologous gene for NADPH-CytP450 reductase, is used for a second round of transformation by cocultivation of plant tissue with *Aarobacterium tumefaciens* strain MOG101 containing the binary vector pMOG712 as described in Example V. Transgenic plants are regenerated from shoots that grow on selection medium, rooted and transferred to germination medium or soil. Young plants are grown to maturity and allowed to self-pollinate and set seed. Plants transgenic for both the sense and the antisense construct are analyzed for reduced susceptibility to PPN as described.

c) Introduction of chimaeric DNA sequences of the 35S promoter and the Squash gene coding for glycerol-3-phosphate acyltransferase Arabidopsis plants are transformed with pMOG719-1 by cocultivation of plant tissue with *Agrobacterium tumefaciens* strain MOG101 containing the binary vector as described in Example V. Transgenic plants are regenerated from shoots that grow on selection medium, rooted and transferred to germination medium or soil. Young plants can be grown to maturity and allowed to self-pollinate and set seed. Homozygous lines are selected through analysis of the offspring by germination of selective medium. The expression level of the heterologous gene is analyzed with Northern blotting.

d) Introduction of chimaeric DNA sequences of the Delta0.3TobRB7 promoter and the antisense glycerol-3-phosphate acyltransferase gene for specific repression of the nematode-induced feeding structures in Arabidopsis.

Arabidopsis plants transgenic for the T-DNA of construct pMOG719-1 is used for a second round of transformation by cocultivation of plant tissue with *Agrobacterium tumefaciens* strain MOG101 containing the binary vector pMOG713 as described in Example V. Transgenic plants are regenerated from shoots that grow on selection medium, rooted and transferred to germination medium or soil. Young plants can be grown to maturity and allowed to self-pollinate and set seed. Plants transgenic for both the sense and the antisense construct are analyzed for reduced susceptibility to PPN as described.

e) Introduction of chimaeric DNA sequences of the 35S promoter and the maize gene coding for adenine nucleotide translocator Tobacco plants are transformed with pMOG719-2 by cocultivation of plant tissue with *Aprobacterium tumefaciens* strain LBA4404 containing the binary vector as described in Example V. Transgenic plants are regenerated from shoots that grow on selection medium, rooted and transferred to germination medium or soil. Young plants can be grown to maturity and allowed to self-pollinate and set seed. Homozygous lines are selected through analysis of the offspring by germination of selective medium. The expression level of the heterologous gene is analyzed with Northern blotting.

f) Introduction of chimearic DNA sequences of the Delta0.3 TobRB7 promoter and the antisense adenine nucleotide translocator gene for specific repression of the nematode-induced feeding structures in potato.

Potato plants transgenic for the T-DNA of the construct pMOG719-2, is used for a second round of transformation by cocultivation of plant tissue with *Agrobacterium tumefaciens* strain LBA4404 containing the binary vector pMOG714 as described in Example V. Transgenic plants are regenerated from shoots that grow on selection medium, rooted, clonally propagated and transferred to soil. Plants transgenic for both the sense and the antisense construct are analyzed for reduced susceptibility to PPN as described.

g) Introduction of chimaeric DNA sequences of the 35S promoter and the maize gene coding for the beta-subunit of ATP synthase Potato plants are transformed with pMOG719–3 by cocultivation of plant tissue with *Agrobacterium tumefaciens* strain LBA4404 containing the binary vector as described in Example V. Transgenic plants are regenerated from shoots that grow on selection medium, rooted and transferred to soil or clonally propagated in vitro. The expression level of the heterologous gene is analyzed with Northern blotting.

h) Introduction of chimaeric DNA sequences of the Delta0.3 TobRB7 promoter and the antisense ATP synthase gene for specific repression of the nematode-induced feeding structures in tobacco.

Tobacco plants transgenic for a construct pMOG719-3, is used for a second round of transformation by cocultivation of plant tissue with *Agrobacterium tumefaciens* strain LBA4404 containing the binary vector pMOG715 as described in Example V. Transgenic plants are regenerated from shoots that grow on selection medium, rooted and transferred to germination medium or soil. Young plants can be grown to maturity and allowed to self-pollinate and set seed. Plants transgenic for both the sense and the antisense construct are analyzed for reduced susceptibility to PPN as described.

EXAMPLE XIX

Analysis of transgenic Arabidopsis plants, resistant to a toxin, for susceptibility to PPN in the presence of a toxic compound Selected plant lines from Example XI, transgenic for construct pMOG25 carrying genes coding for GUS and HPT, both under the control of the CaMV 35S promoter, are germinated on nematode-agar medium (Sijmons et al. 1991, Plant J. 1, 245–254) supplemented with 10–20 $\mu$g/ml hygromycin (1 $\mu$g/ml increments) to establish maximum sublethal hygromycin concentrations for each plant line, as position effects of the integration site of the T-DNA influences the level of expression of the HPT-gene and therefor the level of resistance to hygromycin. New seeds from the selected lines are then germinated on in fresh petridishes with nematodeagar medium with the maximum sublethal hygromycin concentration and inoculated with PPN (Sijmons et al. 1991, Plant J. 1, 245–254). The behaviour of the nematodes is followed daily with an inverted microcope and normal penetration and behaviour inside roots is observed at the early infection stages in the presence of hygromycin. At later stages of infection, significantly reduced number of females develop on roots when grown in hygromycin. The development of the NFS is hindered by the local susceptibility to hygromycin as the result of the down-regulation of the 35S promoter.

---

We claim:

1. A plant comprising cells, including a cell of a nematode feeding structure, that are transformed with a first gene comprising a coding sequence-A which encodes a first molecule that, upon expression, has a disruptive effect on the metabolism of the cell of the nematode feeding structure and with a second gene comprising a coding sequence-B which encodes a second molecule that, upon expression, represses the disruptive effect of the first molecule, wherein a) coding sequence-B is under control of a promoter-B that drives expression of the second molecule in cells of the plant wherein the first molecule is expressed, with the proviso that the promoter-B does not effectively drive expression of the second molecule in the cell of the nematode feeding structure; and b) coding sequence-A is under control of a promoter-A that drives expression of the first molecule at least in the cell of the nematode feeding structure.

2. In a method comprising transforming a plant with a herbicide resistance gene that confers to the plant resistance to a herbicide which is otherwise toxic to the plant, the improvement comprising reducing a susceptibility of the plant to infection by plant parasitic nematodes in soil by (a) placing the herbicide resistance gene under control of a promoter that is expressed in cells of the plant that are contacted with the herbicide in step (c), but which promoter is not effectively expressed in a cell of a nematode feeding structure;

(b) growing the plant in soil wherein plant parasitic nematodes are present; and (c) contacting roots of the plant with a herbicide that is toxic to the cell of the nematode feeding structure in an amount sufficient to prevent or retard formation of the cell of the nematode feeding structure whereby to reduce the susceptibility of the plant to infection by the plant parasitic nematodes.

3. A plant according to claim 1 wherein coding sequence-A encodes barnase, coding sequence-B encodes barstar, and wherein promoter-A is a plant promoter and promoter-B is derived from the CaMV 35S promoter or the rolD promoter.

4. A plant according to claim 1, wherein said first molecule is inhibitory to an endogenous gene that encodes a protein or polypeptide product that is essential for formation or maintenance of the nematode feeding structure.

5. A plant according to claim 1, wherein said coding sequence-A produces an RNA transcript that is complementary to an endogenous gene transcript encoding a protein or polypeptide product essential for formation or maintenance of the nematode feeding structure, wherein said protein or polypeptide product performs a function at least in cells of the plant outside the nematode feeding structure, and wherein said coding sequence-B encodes a protein or polypeptide product that performs the function.

6. A plant according to claim 5, wherein said coding sequence-B is derived from a plant species that is different from the host plant species.

7. A plant according to claim 1, wherein promoter-A is derived from the Delta-0.3TobRB7-5A promoter.

8. A plant according to claim 1 which plant belongs to the family Solanaceae.

9. A plant according to claim 8, which plant is *Solanum tuberosum*.

10. The plant of claim 9, which has reduced susceptibility to a potato cyst nematode.

11. Plant material, comprising flowers, fruit, leaves, pollen, seeds, or tubers, obtained from a plant according to claim 1.

12. A recombinant DNA according to claim 1, wherein said promoter is derived from the Delta-0.3TobRB7-5A or the truncated rolC promoter.

13. A method according to claim 2, wherein the promoter is derived from the cauliflower mosaic virus 35S promoter.

14. A plant as claimed in claim 1 wherein the first molecule is a phytotoxic protein.

15. A method for obtaining plants with reduced susceptibility to invasion by a plant parasitic nematode, the method comprising (a) transforming cells of a plant or progeny of the plant with a coding sequence A and a coding sequence B, said coding sequences A and B being selected such that transformed cells expressing the coding sequences A and B display a normal phenotype and such that a nematode feeding structure comprising a cell expressing the coding sequence A but not expressing the coding sequence B has a reduced ability to support development of the plant parasitic nematode as compared with a nematode feeding structure wherein coding sequence A is not expressed, said coding sequence A being under the control of a promoter A that drives expression of the coding sequence A preferentially in the cell of the nematode feeding structure, said coding sequence B being under the control of a promoter B that drives expression of the coding sequence B in transformed cells wherein coding sequence A is expressed but not in the cell of the nematode feeding structure, (b) generating plants from the transformed cells of step (a); and (c) screening the generated plants for a transformed plant which has a reduced susceptibility to the plant parasitic nematode and which displays the normal phenotype.

16. A method as claimed in claim 15 wherein the transformed cells are formed in step (a) by (i) transforming recipient cells of the plant with said coding sequence B under the control of the promoter B, (ii) generating progeny of the plant from the recipient cells transformed in step (i), and (iii) transforming cells of the progeny that express coding sequence B with the coding sequence A under control of the promoter A.

17. A method as claimed in claim 15, wherein coding sequence A encodes a toxin.

18. A method as claimed in claim 17, wherein coding sequence A encodes a transcript that is complementary to a transcript encoded by an endogenous gene of the nematode feeding structure, said endogenous gene encoding a protein or polypeptide product that is essential for viability of the cell of the nematode feeding structure.

19. A method as claimed in claim 15, wherein promoter A comprises a truncated rolC or a truncated tobacco RB7-5A promoter.

20. A method as claimed in claim 15, wherein coding sequence A encodes a transcript for a ribonuclease.

21. A method as claimed in claim 20, wherein coding sequence B encodes (i) a transcript that is complementary to the transcript encoded by coding sequence A or (ii) a protein that represses the activity of the ribonuclease.

22. A method as claimed in claim 15, wherein step (a) comprises coincubating said cells of the plant or progeny of the plant with an Agrobacterium strain that contains said coding sequence A, said coding sequence B or both.

* * * * *

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 39 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO:1:

```
          GTTTCTACAG GACGGAGGAT CCTGGAAGTA TTTGAAAGA                    39
```

( 2 ) INFORMATION FOR SEQ ID NO: 2:

( i ) SEQUENCE CHARACTERISTICS:
        ( A ) LENGTH: 20 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 2:

```
CAGCTATGAC CATGATTACG                                                  20
```

( 2 ) INFORMATION FOR SEQ ID NO: 3:

( i ) SEQUENCE CHARACTERISTICS:
        ( A ) LENGTH: 36 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 3:

```
CTGCTCGAGC CTAGGCACAG GTTATCAACA CGTTTG                                36
```

( 2 ) INFORMATION FOR SEQ ID NO: 4:

( i ) SEQUENCE CHARACTERISTICS:
        ( A ) LENGTH: 22 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 4:

```
CGGACTCTGG ATCCGGAAAG TG                                               22
```

( 2 ) INFORMATION FOR SEQ ID NO: 5:

( i ) SEQUENCE CHARACTERISTICS:
        ( A ) LENGTH: 27 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 5:

CTTACTCGAG CCATGGTAAG TTTCTGC        27

( 2 ) INFORMATION FOR SEQ ID NO: 6:

( i ) SEQUENCE CHARACTERISTICS:
        ( A ) LENGTH: 22 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 6:

CGGACTCTGG ATCCGGAAAG TG        22

( 2 ) INFORMATION FOR SEQ ID NO: 7:

( i ) SEQUENCE CHARACTERISTICS:
        ( A ) LENGTH: 22 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 7:

CTCCAAATAC TAGCTCAAAA CC        22

( 2 ) INFORMATION FOR SEQ ID NO: 8:

( i ) SEQUENCE CHARACTERISTICS:
        ( A ) LENGTH: 20 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 8:

CCTCACCATG GTTAGTTCTC        20

( 2 ) INFORMATION FOR SEQ ID NO: 9:

( i ) SEQUENCE CHARACTERISTICS:
        ( A ) LENGTH: 28 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 9:

CTTGAATTCT AGATAAGCTT ATCTAAAC 28

( 2 ) INFORMATION FOR SEQ ID NO: 10:

( i ) SEQUENCE CHARACTERISTICS:
        ( A ) LENGTH: 20 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 10:

CCTCACCATG GTTAGTTCTC 20

( 2 ) INFORMATION FOR SEQ ID NO: 11:

( i ) SEQUENCE CHARACTERISTICS:
        ( A ) LENGTH: 25 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 11:

GGCGGATCGG AGCGGGGAGC TGAAG 25

( 2 ) INFORMATION FOR SEQ ID NO: 12:

( i ) SEQUENCE CHARACTERISTICS:
        ( A ) LENGTH: 27 BASE PAIRS
        ( B ) TYPE: NUCLEIC ACID
        ( C ) STRANDEDNESS: SINGLE
        ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 12:

GATACCATGG ATCACCAGAC ATCTCTG 27

( 2 ) INFORMATION FOR SEQ ID NO: 13:

( i ) SEQUENCE CHARACTERISTICS:
        ( A ) LENGTH: 27 BASE PAIRS
        ( B ) TYPE: NUCLEIC ACID
        ( C ) STRANDEDNESS: double
        ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 13:

GGTTCTGGGG ATCCAAAACG TGTCGAG 27

( 2 ) INFORMATION FOR SEQ ID NO: 14:

( i ) SEQUENCE CHARACTERISTICS:
        ( A ) LENGTH: 28 BASE PAIRS
        ( B ) TYPE: NUCLEIC ACID
        ( C ) STRANDEDNESS: SINGLE ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 14:

GGCTTCCATG GTTTCGTTAC CATACATC 28

( 2 ) INFORMATION FOR SEQ ID NO: 15:

( i ) SEQUENCE CHARACTERISTICS:
      ( A ) LENGTH: 25 BASE PAIRS
      ( B ) TYPE: NUCLEIC ACID
      ( C ) STRANDEDNESS: SINGLE
      ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 15:

GCCCGGGATC CGGTTTATCC ACTCG 25

( 2 ) INFORMATION FOR SEQ ID NO: 16:

( i ) SEQUENCE CHARACTERISTICS:
      ( A ) LENGTH: 27 BASE PAIRS
      ( B ) TYPE: NUCLEIC ACID
      ( C ) STRANDEDNESS: SINGLE
      ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 16:

GAGTATTTTC CATGGATTGT GTTTGTG 27

( 2 ) INFORMATION FOR SEQ ID NO: 17:

( i ) SEQUENCE CHARACTERISTICS:
      ( A ) LENGTH: 26 BASE PAIRS
      ( B ) TYPE: NUCLEIC ACID
      ( C ) STRANDEDNESS: SINGLE
      ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 17:

GCTAGCCGGA TCCATCTGAG CTCCAG 26

( 2 ) INFORMATION FOR SEQ ID NO: 18:

( i ) SEQUENCE CHARACTERISTICS:
      ( A ) LENGTH: 29 BASE PAIRS
      ( B ) TYPE: NUCLEIC ACID
      ( C ) STRANDEDNESS: SINGLE
      ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 18:

GACGTCCATG GCTGAATTAG CCACCACCG 29

( 2 ) INFORMATION FOR SEQ ID NO: 19:

(i) SEQUENCE CHARACTERISTICS:
  (A) LENGTH: 28 BASE PAIRS
  (B) TYPE: NUCLEIC ACID
  (C) STRANDEDNESS: SINGLE
  (D) TOPOLOGY: LINEAR (ii) MOLECULE TYPE: cDNA (iii) HYPOTHETICAL: YES (xi) SEQUENCE DESCRIPTION: SEQ ID NO: 19:

CCCTCCAGGA TCCCTTCTCG GAGGCTTC                      28

(2) INFORMATION FOR SEQ ID NO: 20:

(i) SEQUENCE CHARACTERISTICS:
    (A) LENGTH: 28 BASE PAIRS
    (B) TYPE: NUCLEIC ACID
    (C) STRANDEDNESS: SINGLE
    (D) TOPOLOGY: LINEAR (ii) MOLECULE TYPE: cDNA (iii) HYPOTHETICAL: YES (xi) SEQUENCE DESCRIPTION: SEQ ID NO: 20:

GAAAAGAAAG CCATGGAACT TTATAATC                      28

(2) INFORMATION FOR SEQ ID NO: 21:

(i) SEQUENCE CHARACTERISTICS:
    (A) LENGTH: 21 BASE PAIRS
    (B) TYPE: NUCLEIC ACID
    (C) STRANDEDNESS: SINGLE
    (D) TOPOLOGY: LINEAR (ii) MOLECULE TYPE: cDNA (iii) HYPOTHETICAL: YES (xi) SEQUENCE DESCRIPTION: SEQ ID NO: 21:

GCTTCCAGAT CTATGGCGGA G                             21

(2) INFORMATION FOR SEQ ID NO: 22:

(i) SEQUENCE CHARACTERISTICS:
    (A) LENGTH: 23 BASE PAIRS
    (B) TYPE: NUCLEIC ACID
    (C) STRANDEDNESS: SINGLE
    (D) TOPOLOGY: LINEAR (ii) MOLECULE TYPE: cDNA (iii) HYPOTHETICAL: YES (xi) SEQUENCE DESCRIPTION: SEQ ID NO: 22:

GATTACCAAA AGATCTGATG TTG                           23

(2) INFORMATION FOR SEQ ID NO: 23:

(i) SEQUENCE CHARACTERISTICS:
    (A) LENGTH: 34 BASE PAIRS
    (B) TYPE: NUCLEIC ACID
    (C) STRANDEDNESS: SINGLE
    (D) TOPOLOGY: LINEAR (ii) MOLECULE TYPE: cDNA (iii) HYPOTHETICAL: YES (xi) SEQUENCE DESCRIPTION: SEQ ID NO: 23:

GAATTCGGAT CCTGATGCCA GACCCCGCTC TGTG 34

( 2 ) INFORMATION FOR SEQ ID NO: 24:

( i ) SEQUENCE CHARACTERISTICS:
       ( A ) LENGTH: 25 BASE PAIRS
       ( B ) TYPE: NUCLEIC ACID
       ( C ) STRANDEDNESS: SINGLE
       ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 24:

GGACCGGGAT CCCACACTGC TCTTG 25

( 2 ) INFORMATION FOR SEQ ID NO: 25:

( i ) SEQUENCE CHARACTERISTICS:
       ( A ) LENGTH: 24 BASE PAIRS
       ( B ) TYPE: NUCLEIC ACID
       ( C ) STRANDEDNESS: SINGLE
       ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 25:

CCCTGGATCC GGACCGGCCA TGGC 24

( 2 ) INFORMATION FOR SEQ ID NO: 26:

( i ) SEQUENCE CHARACTERISTICS:
       ( A ) LENGTH: 25 BASE PAIRS
       ( B ) TYPE: NUCLEIC ACID
       ( C ) STRANDEDNESS: SINGLE
       ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 26:

CAAGCAAGGA TCCTCCTTAT GAAGC 25

( 2 ) INFORMATION FOR SEQ ID NO: 27:

( i ) SEQUENCE CHARACTERISTICS:
       ( A ) LENGTH: 21 BASE PAIRS
       ( B ) TYPE: NUCLEIC ACID
       ( C ) STRANDEDNESS: SINGLE
       ( D ) TOPOLOGY: LINEAR ( i i ) MOLECULE TYPE: cDNA ( i i i ) HYPOTHETICAL: YES ( x i ) SEQUENCE DESCRIPTION: SEQ ID NO: 27:

CCAGACTGAA TGCCCACAGG C 21

( 2 ) INFORMATION FOR SEQ ID NO: 28:

( i ) SEQUENCE CHARACTERISTICS:
       ( A ) LENGTH: 20 BASE PAIRS
       ( B ) TYPE: NUCLEIC ACID
       ( C ) STRANDEDNESS: SINGLE
       ( D ) TOPOLOGY: LINEAR

-continued

```
    (  i  i  )  MOLECULE TYPE: cDNA (  i  i  i  )  HYPOTHETICAL: YES (  x  i  )  SEQUENCE DESCRIPTION: SEQ ID NO: 28:

GGTGACGCAT GTCGCGCAAG                                                                  20

( 2 ) INFORMATION FOR SEQ ID NO: 29:

(  i  )  SEQUENCE CHARACTERISTICS:
            ( A ) LENGTH: 15 AMINO ACIDS
            ( B ) TYPE: AMINO ACID
            ( C ) STRANDEDNESS: SINGLE
            ( D ) TOPOLOGY: LINEAR (  i  i  )  MOLECULE TYPE: PEPTIDE (  i  i  i  )  HYPOTHETICAL: YES (  x  i  )  SEQUENCE DESCRIPTION: SEQ ID NO: 29:

Ala  Glu  Ser  Val  Leu  Gln  Val  Phe  Arg  Glu  Ala  Lys  Ala  Glu  Gly
    1                   5                        10                       15

( 2 ) INFORMATION FOR SEQ ID NO: 30:

(  i  )  SEQUENCE CHARACTERISTICS:
            ( A ) LENGTH: 15 AMINO ACIDS
            ( B ) TYPE: AMINO ACID
            ( C ) STRANDEDNESS: SINGLE
            ( D ) TOPOLOGY: LINEAR (  i  i  )  MOLECULE TYPE: PEPTIDE (  i  i  i  )  HYPOTHETICAL: YES (  x  i  )  SEQUENCE DESCRIPTION: SEQ ID NO: 30:

Arg  Gln  Phe  Glu  Gln  Ser  Lys  Gln  Leu  Thr  Glu  Asn  Gly  Ala  Glu
    1                   5                        10                       15

( 2 ) INFORMATION FOR SEQ ID NO: 31:

(  i  )  SEQUENCE CHARACTERISTICS:
            ( A ) LENGTH: 15 AMINO ACIDS
            ( B ) TYPE: AMINO ACID
            ( C ) STRANDEDNESS: SINGLE
            ( D ) TOPOLOGY: LINEAR (  i  i  )  MOLECULE TYPE: PEPTIDE (  i  i  i  )  HYPOTHETICAL: YES (  x  i  )  SEQUENCE DESCRIPTION: SEQ ID NO: 31:

Leu  Lys  Lys  Glu  Leu  Ala  Leu  Pro  Glu  Tyr  Tyr  Gly  Asn  Leu  Asp
    1                   5                        10                       15
```